United States Patent [19]

Kim et al.

[11] Patent Number: 5,736,628
[45] Date of Patent: Apr. 7, 1998

[54] BENZENESULFONYLUREA DERIVATIVES

[75] Inventors: Dae-Whang Kim; Young Kwan Ko; Jin-Seog Kim; Dong Whan Ku, all of Daejeon, Rep. of Korea

[73] Assignee: Korea Research Institute of Chemical Technology, Daejeon, Rep. of Korea

[21] Appl. No.: 477,737

[22] Filed: Jun. 7, 1995

Related U.S. Application Data

[62] Division of Ser. No. 117,076, filed as PCT/KR92/00007, Mar. 9, 1992, Pat. No. 5,461,025.

[30] Foreign Application Priority Data

Mar. 8, 1991 [KR] Rep. of Korea .................. 1991-3704

[51] Int. Cl.$^6$ .................. C07D 251/46; C07D 251/52
[52] U.S. Cl. .................. 544/211; 544/113; 544/212; 544/197; 544/198; 544/206; 544/207; 544/208; 544/209; 544/219
[58] Field of Search .................. 504/212, 213; 544/113, 211, 212, 197, 198, 206, 207, 208, 209, 219

[56] References Cited

U.S. PATENT DOCUMENTS 4,786,314  11/1988  Artz .................. 504/214

FOREIGN PATENT DOCUMENTS 44209   1/1982   European Pat. Off. .
125205  11/1984  European Pat. Off. .

*Primary Examiner*—John M. Ford
*Attorney, Agent, or Firm*—Kenyon & Kenyon

[57] ABSTRACT

The present invention is directed to novel benzenesulfonylurea derivatives having herbicidal activity. The benzenesulfonylurea derivatives have the following general formula (I):

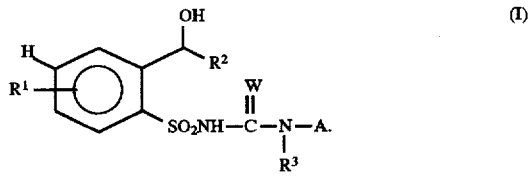

6 Claims, No Drawings

BENZENESULFONYLUREA DERIVATIVES

This application is a division application of application Ser. No. 08/117,076, filed Dec. 9, 1993, now U.S. Pat. No. 5,461,025 which is an application filed under 35 U.S. C. § 371 of PCT/KR92/00007, filed Mar. 9, 1992.

TECHNICAL FIELD

The present invention relates to novel benzenesulfonylurea derivatives having agriculturally suitable for herbicidal activity.

BACKGROUND OF THE INVENTION

It is publicly well known that sulfonyl urea derivatives have a herbicidal activity. Here are the formulas for the sulfonyl ureas.

1) U.S. Pat. No. 4,332,611 discloses the compound having the following formula

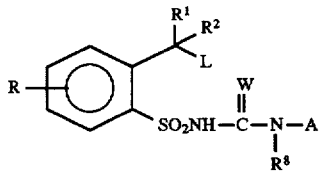

wherein,

L is OH,

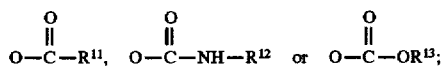

R is H, F, Cl, Br, $NO_2$, $CF_3$ or $C_1$–$C_3$ alkyl or alkoxy;
$R^1$ is H or $C_1$–$C_4$ alkyl;
$R^2$ is H or $CH_3$;
$R^8$ is H, $CH_3$ or $OCH_3$;
$R^{11}$ is H, $C_1$–$C_5$ alkyl, $C_2$–$C_3$ alkenyl or $C_2$–$C_3$ alkynyl;
A is pyrimidine or triazine.

2) U.S. Pat. No. 4,786,314 discloses the compound having the following formula

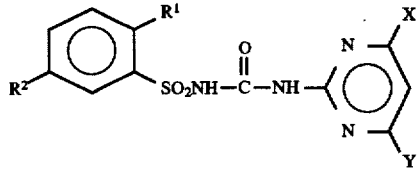

wherein, $R^1$ is F, Cl, Br, $NO_2$, $C_1$–$C_4$ alkyl, $C_2$–$C_4$ alkenyl, $C_2$–$C_4$ haloalkenyl, $C_2$–$C_4$ alkynyl, $C_1$–$C_4$ haloalkyl, $C_1$–$C_4$ alkoxy or $C_1$–$C_2$ alkyl substituted with OH, alkoxy, alkylthio, phenyl or $CH_2CN$;
$R^2$ is

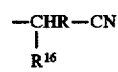

etc ($R^{16}$ is alkyl);
X is alkyl, alkoxy, etc.
Y is alkyl, alkoxy, halogen, etc.

3) U.S. Pat. No. 4,838,926 discloses the compound having the following formula

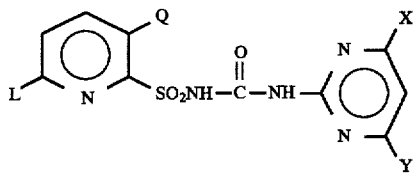

wherein,
Q is $C_1$–$C_4$ alkyl substituted with $R^2$;
$R^2$ is $OR^3$,

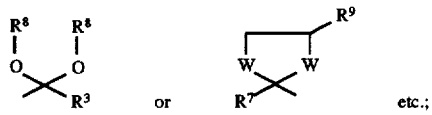

$R^3$ is H, $C_1$–$C_4$ alkyl, alkenyl, alkynyl or haloalkyl etc.;
L is

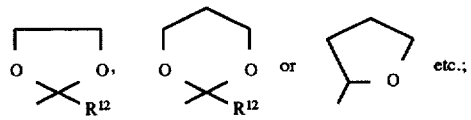

$R^{12}$ is H or $CH_3$.

4) European Patent No. 125,205 discloses the compound having the following formula

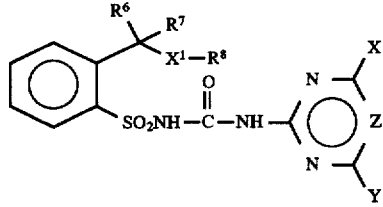

wherein,
$R^6$ is H, alkyl or F;
$R^7$ is H or $CH_3$;
$X^1$ is O or S;
$R^8$ is haloalkyl or alkoxyalkyl.

5) U.S. Pat. No. 4,348,220 discloses the compound having the following formula

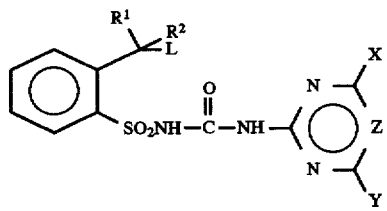

wherein,
L is $OR^9$;
$R^1$ is H or $C_1$–$C_4$ alkyl;
$R^2$ is H or $CH_3$;
$R^9$ is $C_1$–$C_6$ alkyl, $C_3$–$C_4$ alkenyl or $C_3$–$C_6$ cycloalky.

As the above patents, many sulfonyl urea herbicides have known until recently.

Even with these herbicides, more and more weeds develop immunity forwards these herbicides and cause undesirable vegetations. Thus, continuous research is in demand to develop more effective and newer for a good harvest.

Therefore, the object of the presentation is to invent a new benzenesulfonylurea derivative having a very prominent herbicidal activity with a good selectivity for various vegetations and agriculturally suitable herbicides for treatment of pre-emergence and/or post-emergence or plant growth regulants.

SUMMARY OF THE INVENTION

The present invention relates to novel benzenesulfonylurea derivatives having the following general formula (I)

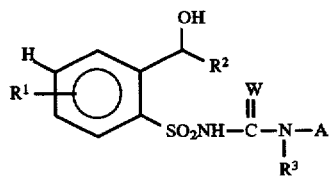

wherein, $R^1$ is H, $C_1$–$C_3$ alkyl, $C_1$–$C_3$ haloalkyl, halogen, CN, $NO_2$, $C_1$–$C_3$ alkoxy, $C_1$–$C_3$ haloalkoxy, $SO_2NR'R''$, $C_1$–$C_3$ alkylthio, $C_1$–$C_3$ alkylsulfinyl, $C_1$–$C_3$ alkylsulfonyl, $SCH_2F$, $NH_2$, $NHCH_3$, $N(Me)_2$, $C_1$–$C_2$ alkyl substituted with $C_1$–$C_2$ alkoxy, $C_1$–$C_2$ haloalkoxy, SH, $SCH_3$, CN or OH or $CO_2R'''$; and then $R'$ is H, $C_1$–$C_4$ alkyl, $C_2$–$C_3$ cyanoalkyl, methoxy or ethoxy; $R''$ is H, $C_1$–$C_4$ alkyl, $C_3$–$C_4$ alkenyl, or when taken together connecting $R'$ and $R''$, —$(CH_2)_3$—, —$(CH_2)_4$—, —$(CH_2)_5$— or $CH_2CH_2OCH_2CH_2$—, may be formed;

$R'''$ is $C_1$–$C_4$ alkyl, $C_3$–$C_4$ alkenyl, $C_3$–$C_4$ alkynyl, $C_1$–$C_4$ alkyl substituted with 1–3 halogens or cyano groups, $C_5$–$C_6$ cycloalkyl, $C_4$–$C_7$ cycloalkylalkyl or $C_2$–$C_4$ alkoxyalkyl;

$R^2$ is $C_1$–$C_6$ alkyl substituted with 1–3 halogens;

$R^3$ is H or $CH_3$;

W is O or S;

A is A1, A2, A3, A4, A5, A6 or A7 as followings;

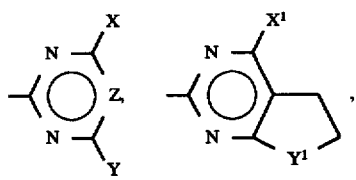

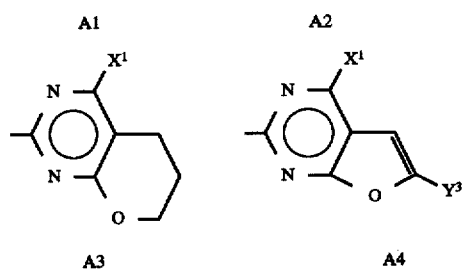

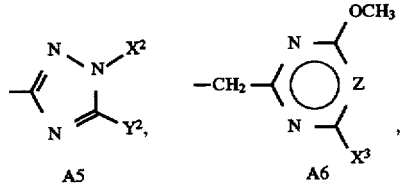

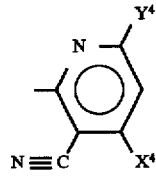

wherein,

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino, di($C_1$–$C_3$ alkyl) amino or $C_3$–$C_5$ cycloalkyl;

Y is H, $C_1$–$C_4$ alkyl, $C_1$–$C_4$ alkoxy, $C_1$–$C_4$ haloalkoxy, $C_1$–$C_4$ haloalkyl, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_1$–$C_4$ haloalkyl, $C_2$–$C_4$ alkynyl, azido, cyano, $C_2$–$C_5$ alkylsulfinylalkyl, $C_2$–$C_5$ alkylsulfonylalkyl, $CH_2OH$, $C_3$–$C_5$ cycloalkyl, $C_3$–$C_5$ cycloalkoxy,

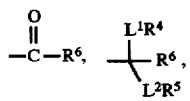

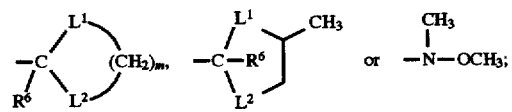

m is 2 or 3;

$L^1$ and $L^2$ are independently O or S;

$R^4$ and $R^5$ are independently $C_1$–$C_2$ alkyl;

$R^6$ is H, or $CH_3$;

Z is CH, N, $CCH_3$ or $CC_2H_5$;

$Y^1$ is O or $CH_2$;

$X^1$ is $CH_3$, $OCH_3$, $OC_2H_5$ or $OCHF_2$;

$Y^2$ is $CH_3$, $CH_2CH_3$, $OCH_3$, $OCH_2CH_3$, $SCH_3$ or $SCH_2CH_3$;

$X^2$ is $CH_3$, $CH_2CH_3$, or $CH_2CF_3$;

$Y^3$ is H or $CH_3$;

$X^3$ is $CH_3$ or $OCH_3$;

$Y^4$ is $CH_3$, $OCH_3$, $OC_2H_5$, $CH_2OCH_3$ or Cl;

$X^4$ is $CH_3$, $OCH_3$, $OC_2H_5$, $CH_2OCH_3$ or Cl;

and these may be an agriculturally suitable salt, and then, (1) if X is Cl, Br, F or I, Z is CH and Y is $OCH_3$, $OC_2H_5$, $NCH_3(OCH_3)$, $NH_2$, $NHCH_3$, $N(CH_3)_2$ or $OCHF_2$;

(2) if X or Y is $OCHF_2$, Z is CH;

(3) $X^4$ and Y4 are not Cl simultaneously;

(4) if W is S, $R^3$ is H, A is $A_1$, Z is CH or N and, Y is $CH_3$, $OCH_3$, $OCH_2CH_3$, $CH_2OCH_3$, $C_2H_5$, $CF_3$, $SCH_3$, $OCH_2CH{=}CH_2$, $OCH_2C{\equiv}CH$, $OCH_2CH_2OCH_3$, $CH(OCH_3)_2$ or

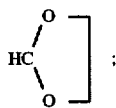

(5) if a number of total carbon atoms of X and Y is more than 4, a number of carbon atoms of $R^2$ is 4 or less than 4.

DETAILED DESCRIPTION OF THE INVENTION

Among the definitions according to the present invention, the following terms have the following meanings;

a) "Alkyl" used ether alone or in compound word such as "alkylthio" or "haloalkyl" etc. denotes straight chain or branched alkyls such as methyl, ethyl, n-propyl, isopropyl or buthyl isomers.

b) "Alkoxy" denotes methoxy, ethoxy, n-propoxy, isopropoxy or buthoxy isomers.

c) "Alkenyl" denotes straight chain or branched alkenes, for example, vinyl, 1-prophenyl, 2-prophenyl, or buthenyl, pentenyl, hexenyl or heptenyl isomers etc.

d) "Alkynyl" denotes straight chain or branched alkynyl such as ethynyl, 1-propynyl, 2-propynyl, or buthynyl, pentynyl or hexynyl isomers.

e) "Halogen" used ether alone or in compound ward "halo" denotes chlorine, fluorine, bromine or iodine.

A preferred group of pyridine sulfonyl urea derivatives having the formula(I) shown as the below, in view of compounding of the polymer and herbicidal activity, wherein (1) $R^3$ is H, W or O;

(2) $R^1$ is H, F, Cl, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $CH_2OCH_3$ or $CH_2SCH_3$;

(3) X is $CH_3$, $OCH_3$, $OCH_2CH_3$, Cl, F, Br, $OCHF_2$, $CH_2F$, $OCH_2CH_2F$, $OCH_2CHF_2$, $OCH_2CF_3$, $CF_3$, $CH_2Cl$ or $CH_2Br$;

Y is H, $C_1$–$C_3$ alkyl, $OCH_3$, $OCH_2CH_3$, $CH_2OCH_3$, $NHCH_3$, $NCH_3(OCH_3)$, $N(CH_3)_2$, $CF_3$, $SCH_3$, $OCH_2CH{=}CH_2$, $OCH_2CH{\equiv}CH$, $CH_2OC_2H_5$, $OCH_2CH_2OCH_3$, $CH_2SCH_3$, $OCHF_2$, $SCHF_2$, cyclopropyl, $C{\equiv}CH$, or $C{\equiv}C$—$CH_3$;

(4) $R^2$ is $CH_2F$, $CHF_2$, $CHFCl$, $CH_2Cl$, $CH_2Br$, $CHFCH_3$, $CH_2CH_2F$, $CH_2CH_2Cl$, $CHClCH_3$, $CHCl_2$, $CHFCH_2F$, $CHClCH_2Cl$, $CHFCH_2Cl$ or $CH_2CF_3$;

(5) A is $A_1$, and Z is CH;

X is $CH_3$, $OCH_3$, $OCH_2CH_3$, Cl or $OCHF_2$;

Y is $CH_3$, $C_2H_5$, $OCH_3$, $CH_2OCH_3$, $CH(OCH_3)_2$, $OCHF_2$, $NHCH_3$, $N(Me)_2$ or cyclopropyl, and $R^1$ is H, $CH_3$, $OCH_3$ or Cl.

A Special group of benzenesulfonylurea derivatives having the formula(I) shown as following compounds, in view of compounding of the polymer and herbicidal activity;

N-[(4,6-dimethoxypyrimidin-2-yl)aminocarbonyl]-2-(2-fluoro-1-hydroxyethyl)benzenesulfonamide, 2-(2-fluoro-1-hydroxyethyl)-N-[(4-methoxy-6-methylpyrimidin-2-yl)aminocarbonyl] benzenesulfonamide, 2-(2-chloro-1-hydroxyethyl)-N-[(4,6-dimethoxypyrimidin-2-yl)aminocarbonyl]benzenesulfonamide, N-[(4,6-dimethoxyprimidin-2-yl)aminocarbonyl]-2-(2-fluoro-1-hydroxy-n-propyl)benzenesulfonamide, 2-(2-chloro-1-hydroxy-n-propyl)-N-[(4,6-dimethoxypyrimidin-2-yl)aminocarbonyl] benzenesulfonamide, 2-(2,2-difluoro-1-hydroxyethyl)-N-[(4,6-dimethoxypyrimidin-2-yl)aminocarbonyl] benzenesulfonamide, etc.

In the above compounds, N-[(4,6-dimethoxypyrimidin-2-yl)aminocarbonyl]-2-(2-fluoro-1-hydroxypropyl) benzenesulfonamide existing to two diastereomeric isomers, has stronger herbicidal activity in paddy field, when the compound has high m.p. (189°–191° C.) in comparison with the compound of low m.p. (166°–168° C.).

The novel compounds having the above formula(I) according to the present invention have a very strong herbicidal activity and a good selectivity for a useful vegetation.

The compounds of the present invention can be prepared by reactions as described in herein below.

The compounds of general formula(I) can be obtained by hydrolyzing the compounds of following formula(II) with alkali under water, organic solvent or the mixture solution thereof.

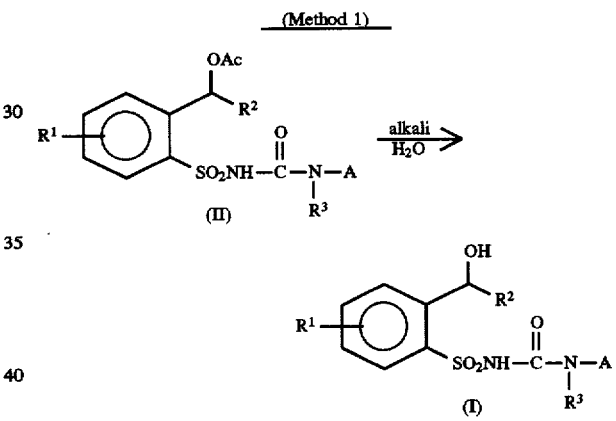

In the above reaction scheme of Method 1, Ac is acetyl group, but it may be a protecting group easily dissolved by acid, alkali or others. In order to hydrolyze the above Ac group, alkali base such as NaOH, KOH, LiOH, $Na_2CO_3$, $K_2CO_3$, etc., preferably LiOH, may be used.

The above reaction of Method I is carried out under water or organic solvent, and also a mixture of water with unreacting solvent such as methanol, ethanol, acetone or THF etc., or solvent alone.

The hydrolysis in the reaction occurs at the temperature of 0°–80° C. and the reaction time of 1–24 hours, and then the obtained product may be easily seperated by acidifying with HCl water solution.

As an other process, after acidifying, the obtained product is extracted with methylene chloride, ethyl acetate, etc. then concentrated/crystalized to obtain the final product. If necessary, a pure product can be obtained by purification to column chromatograph.

The compounds of the above formula(I) according to the present invention can be prepared by reacting the compounds having the following formula(III) with alkali at the temperature of 25°–40° C.

(Method 2)

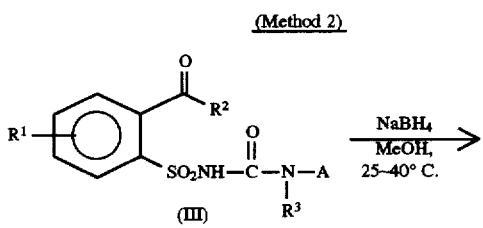

The reaction of process Method 2 may be preferably carried out under alkali such as NaOH etc. of a small quantity. The product may be seperated as the same with the above Method I.

On the other hand, the compound of the above formula(II) used in the present invention can be prepared by reacting the compound of following formula(IV) with formula(V).

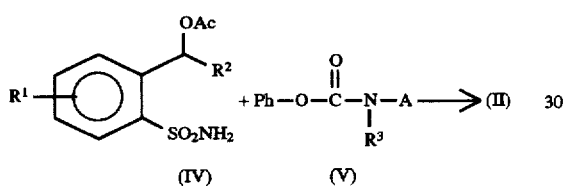

The above reaction may be carried out in solvent such as dioxane, acetonitryl, THF, acetone, MC, toluene or butanone, and then the solvent can be used with small amount of strong base such as Dabco(1,4-diazabicyclo [2.2.2]octane), DBU(1,8-diazabicyclo[5.4.0]undece-7-ene), etc., while reacting at temperature of 20°~80° C.

This reaction discloses on U.S. Pat. No. 4,443,245, and thereafter the final product may be obtained by treatment with acid as the method disclosed on European Patent No. 44,870.

The above compound of formula(III) may be manufactured by the method disclosed on U.S. Pat. No. 4,370,480.

The compounds of general formula(I) can be obtained by reaction the compound of above formula(IV) protected by t-butyldimethylsilane with phenyl carbamate of the above formula(V).

(Method 3)

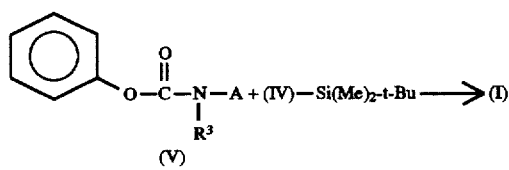

The above reaction may be carried out by adding tetrabutylammonium fluoride in the mixture of carbamate and sulfonamide to obtain the desired product.

In order to prepare carbamate of the above formula(V), amine of below formula(VI) is reacted with diphenylcarbonate or phenylchloroformate under the presence of base as following reaction process.

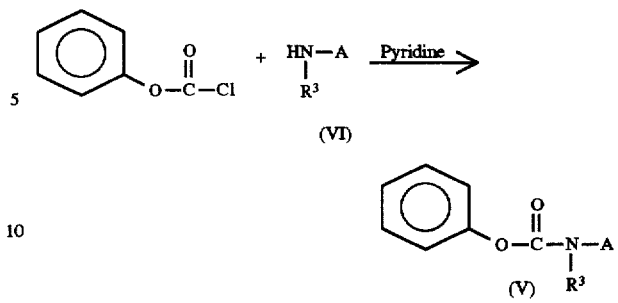

On the other hand, the compound of the above formula (IV) can be prepared by the following reaction process.

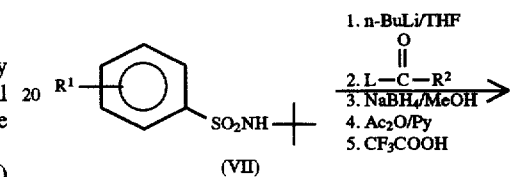

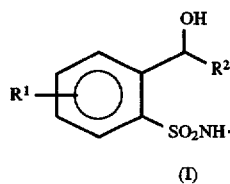

In the above reaction, 2 equivalents of n-butyl lithium is added in t-butylsulfonamide under THF solution at the temperature of $-80°$~$+50°$ C. for 1~24 hrs to obtain dilithio salt, and thereafter

is added while maintaining the temperature of $-70°$~$-80°$ C. to produce kotone compound. In the above, L is alkoxy, $N(CH_3)_2$, $NCH_3(OCH_3)$, etc.

A method for directly lithiating arylsulfonamide discloses on J. G. Lombardino, J. Org. Chem., 36, 1843(1971), and also stowell, J. C. "Carbanions in Org. Synthesis", John Wiley & Sons; New York, 1979; Snieckus, V. Tetrahedron Lett. 26, 1145(1985) and ibid, 1149(1985).

It is well known reactions which the lithiated carban ions get up acylation, and hydroxy compound is obtained by reducing ketone with $LiAlH_4$ or $NaBH_4$.

A reaction of O-acylation is carried out by reacting the obtained hydroxy compound with acetic anhydride under the presence of pyridine, and easily by use of DMAP as a catalyst. The obtained N-t-butyl-sulfonamide is reacted with trifluoroacetic acid, and then t-butyl group is separated to obtain primary sulfonamide of formula(IV).

This process may be easily carried out by a skill person in field of organic compounding technology in accordance with the method disclosed on J. D. Catt and W. L. Matier, J. Org. Chem., 39, 566(1974), ibid 38, 1974(1973), or in the case of treatment of polyphosphoric acid, J. G. Lombardino, J. Org. Chem., 36, 1843(1971). Then, an excess amount(about 0.3M) of trifluoro acetic acide is used, and the reacting solution is stirred at the temperature of 0°~50° C. for 1~72 hrs.

The volatile material of the obtained product is evaporated under vacuum, and then the residue is crystalized in solvent such as diethylether, ethylacetate, etc. In the above reaction process, R1 is a functional group which is stable for high reactive reagent.

The heterocyclic amine compound of formula(VI) may be prepared by a skill person in this technical field from a method disclosed in literatures or the simple transformation of it.

For example, European Patent Application No. 84,244 (Pub. Jul. 27, 1983) and J. Am. Chem. Soc., 69,3072(1947) of W. Braker et al. discloses a method for preparing aminopyrimidine and triazine substituted with acetyl group. European Patent No. 72,347 and U.S. Pat. Nos. 4,443,243/ 4,487,915 disclose a method for preparing aminopyrimidine and/or triazine substituted with haloalkyl such as $OCHF_2$, $SCHF_2$, $OCH_2CH_2F$ and $OCH_2CF_3$, etc. and haloalkylthio as a substitution group.

European Patent No. 108,708, U.S. Pat. Nos. 4,515,626/ 4,600,428 disclose cyclopropylpyrimidine and/or triazine substituted with alkyl, haloalkyl, alkoxy, haloalkoxy, alkylamino, dialkylamio and alkoxyalkyl group etc.

European Patent No. 15,863 discloses a method for preparing the compound of the above formula(VI), as 5,6-dihydro-puro[2,3-d]pyrmidine-2-amine compounds and cyclopenta[d]pyrimidine-2-amine compounds which A is $A_2$; and 6,7-dihydro-5H-pyrano-[2,3-d]pyrimidine-2-amine compound which A is $A_3$.

European Patent No. 46,677 discloses puro[2,3-d]pyridine-2-amine compounds which A is $A_4$ in the formula (VI), and European Patent No. 73,562 discloses heterocyclic compounds which A is $A_5$.

The compound of formula(VI) which A is $A_6$ can be prepared by European Patent No. 94,260. The compound of formula(VI) which A is $A_7$ can be manufactured by the method of European Patent No. 125,864.

Common methods for preparing aminopyridine and triazine compounds are arranged on the following literatures:

"The chemistry and Heterocyclic compounds", Series, Interscience Publishers, Inc., New York and London; "Pyrimidines", Vol. 16, D. J. Brown Ed.; "S-Triazines and Derivatives", Vol. 13, E. M. Sinolin and L. Rapaport. Composition of triazine compounds is disclosed in F. C. Schaefer, U.S. Pat. No. 3,154,547 and K. R. Huffman and F. C. Schaefer, J. Org. Chem., 28, 1812(1963).

On the other hand, salts of the compound of the above formula(I) also are useful as herbicide, and they can be prepared by various methods according to prior art.

For example, metal salts of the compound can be prepared by reacting the above formula(I) compound with strong basic anion, e.g. alkali or alkaline earth metal solution having hydroxyl group, alkoxide or carbonate, and also quaternary amine salt alike.

A salt of the formula(I) compound may also be obtained by cation exchange. The cation exchange can be manfactured by directly reacting solution containing cation for exchange with solution of salt of formula(I), for example, solution of alkali metal or quaternary amine salt.

This method is useful when the desired salt is water insoluble, for example, copper salt is separarated by filtering.

This ion exchange may be carried out by passing through a column of cation exchange resin with solution of salt of the formula(I), for example, alkaline metal or quartermary amine salt solution.

This method is useful when the desirable salt is water soluble, especially sodium, potassium or calcium salt.

The above manufacturing methods am summarized briefly, but the methods can be easily carried out by a skill person in this technical field of composition and manufacturing for sulfonyl urea or organic composition.

The compounds of the above general formula(I) according to the present invention specify as the following Tables 1~9;

TABLE 1

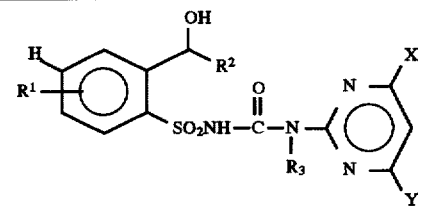

| $R^1$ | $R^2$ | $R^3$ | X | Y | mp (°C.) |
|---|---|---|---|---|---|
| H | $CH_2F$ | H | $OCH_3$ | $OCH_3$ | 180–181 |
| H | $CH_2F$ | H | $CH_3$ | $OCH_3$ | 153–155 |
| H | $CH_2F$ | H | $CH_3$ | $CH_3$ | 148–150 |
| H | $CH_2F$ | H | Cl | $OCH_3$ | |
| H | $CH_2F$ | H | Br | $OCH_3$ | |
| H | $CH_2F$ | H | H | $CH_3$ | |
| H | $CH_2F$ | H | $OCH_3$ | H | |
| H | $CH_2F$ | H | $OCH_3$ | $CH_2OC_2H_5$ | |
| H | $CH_2F$ | H | $OCF_2H$ | $OCH_3$ | |
| H | $CH_2F$ | H | $OCH_3$ | $CH(OCH_3)_2$ | |
| H | $CH_2F$ | H | $CH_3$ | $OC_2H_5$ | |
| H | $CH_2F$ | H | $CH_3$ | $CH_2OCH_3$ | |
| H | $CH_2F$ | H | $OCH_3$ | $CH_2OCH_3$ | |
| H | $CH_2F$ | H | $C_2H_5$ | $OCH_3$ | |
| H | $CH_2F$ | H | $OC_2H_5$ | $OCH_3$ | |
| H | $CH_2F$ | H | $OCH_2CF_3$ | $OCH_3$ | |
| H | $CH_2F$ | H | $CF_3$ | $OCH_3$ | |
| H | $CH_2F$ | H | $CH_2F$ | $OCH_3$ | |
| H | $CH_2F$ | H | $CH_2Cl$ | $OCH_3$ | |
| H | $CH_2F$ | H | $CH_2Br$ | $OCH_3$ | |

TABLE 1-continued

| R¹ | R² | R³ | X | Y | mp (°C.) |
|---|---|---|---|---|---|
| H | CH₂F | H | F | OCH₃ | |
| H | CH₂F | H | I | OCH₃ | |
| H | CH₂F | H | OCH₂CH₂F | OCH₃ | |
| H | CH₂F | H | OCH₂CH₂CF₃ | OCH₃ | |
| H | CH₂F | H | OCH₂CHF₂ | CH₃ | |
| H | CH₂F | H | OCH₂CF₃ | CH₃ | |
| H | CH₂F | H | Cl | OC₂H₅ | |
| H | CH₂F | H | OC₂H₅ | NHCH₃ | |
| H | CH₂F | H | OC₂H₅ | CH₂SCH₃ | |
| H | CH₂F | H | OCF₂H | CH₃ | |
| H | CH₂F | H | Cl | OCF₂H | |
| H | CH₂F | H | NH₂ | OC₂H₅ | |
| H | CH₂F | H | n-C₃H₇ | OCH₃ | |
| H | CH₂F | H | NHCH₃ | OCH₃ | |
| H | CH₂F | H | OCH₃ | SCH₃ | |
| H | CH₂F | H | OCH₃ | SCF₂H | |
| H | CH₂F | H | OCH₃ | OCH₂C≡CH | |
| H | CH₂F | H | OCH₃ | OCH₂CH=CH₂ | |
| H | CH₂F | H | OCH₃ | C≡CH | |
| H | CH₂F | H | OCH₃ | N(CH₃)₂ | |
| H | CH₂F | H | OCH₃ | cyclopropyl | |
| H | CH₂F | H | OCH₃ | NH₂ | |
| H | CH₂F | H | OCH₃ | CF₃ | |
| H | CH₂F | H | OCH₃ | OCH₂CH₂OCH₃ | |
| H | CH₂F | H | OCH₃ | CH₂SCH₃ | |
| H | CH₂F | H | OCH₃ | CHO | |
| H | CH₂F | H | OCH₃ | COCH₃ | |
| H | CH₂F | H | OCH₃ | CH(SCH₃)OC₂H₅ | |
| H | CH₂F | H | OCH₃ | C(CH₃)(SCH₃)₂ | |
| H | CH₂F | H | OCH₃ | C(SC₂H₅)₂ | |
| H | CH₂F | H | OCH₃ | 1,3-dioxolan-2-yl | |
| H | CH₂F | H | OCH₃ | 2-methyl-1,3-oxathiolan-2yl | |
| H | CH₂F | H | OCH₃ | 1,3-oxathian-2-yl | |
| H | CH₂F | H | OCH₃ | 2-methyl-1,3-dithian-2-yl | |
| H | CH₂F | H | OCH₃ | 4-methyl-1,3-dioxolan-2-yl | |
| H | CH₂F | H | OCH₃ | 2-4-dimethyl-1,3-dithiolan-2-yl | |
| H | CH₂F | H | OCH₃ | N(OCH₃)(CH₃) | |
| H | CH₂F | H | OCH₃ | C≡CCH₃ | |
| H | CH₂F | H | OCH₃ | C₂H₅ | |
| H | CH₂F | H | OCH₃ | OCF₂Br | |
| H | CHFCH₃ | H | OCH₃ | OCH₃ | 189–191 (high mp) |
| H | CHFCH₃ | H | OCH₃ | OCH₃ | 166–168 (low mp) |
| H | CHFCH₃ | H | CH₃ | OCH₃ | 147–149 |
| H | CHFCH₃ | H | CH₃ | CH₃ | |
| H | CHFCH₃ | H | Cl | OCH₃ | |
| H | CHFCH₃ | H | Br | OCH₃ | |
| H | CHFCH₃ | H | CH₃ | H | |
| H | CHFCH₃ | H | OCH₃ | H | |
| H | CHFCH₃ | H | OCH₃ | CH₂OC₂H₅ | |
| H | CHFCH₃ | H | OCF₂H | OCH₃ | |
| H | CHFCH₃ | H | OCH₃ | CH(OCH₃)₂ | |
| H | CHFCH₃ | H | CH₃ | OC₂H₅ | |
| H | CHFCH₃ | H | CH₃ | CH₂OCH₃ | |
| H | CHFCH₃ | H | OCH₃ | CH₂OCH₃ | |
| H | CHFCH₃ | H | OCH₃ | C₂H₅ | |
| H | CHFCH₃ | H | OC₂H₅ | OCH₃ | |
| H | CHFCH₃ | H | OCH₂CF₃ | OCH₃ | |
| H | CHFCH₃ | H | CF₃ | OCH₃ | |
| H | CHFCH₃ | H | CH₂F | OCH₃ | |

TABLE 1-continued

| R¹ | R² | R³ | X | Y | mp (°C.) |
|---|---|---|---|---|---|
| H | CHFCH₃ | H | CH₂Cl | OCH₃ | |
| H | CHFCH₃ | H | CH₂Br | OCH₃ | |
| H | CHFCH₃ | H | F | OCH₃ | |
| H | CHFCH₃ | H | I | OCH₃ | |
| H | CHFCH₃ | H | OCH₂CH₂F | OCH₃ | |
| H | CHFCH₃ | H | OCH₂CH₂CF₃ | OCH₃ | |
| H | CHFCH₃ | H | OCH₂CHF₂ | CH₃ | |
| H | CHFCH₃ | H | OCH₂CF₃ | CH₃ | |
| H | CHFCH₃ | H | Cl | OC₂H₅ | |
| H | CHFCH₃ | H | OC₂H₅ | NHCH₃ | |
| H | CHFCH₃ | H | OCH₃ | CH₂SCH₃ | |
| H | CHFCH₃ | H | OCF₂H | CH₃ | |
| H | CHFCH₃ | H | Cl | OCF₂H | |
| H | CH₂CH₂F | H | OCH₃ | OCH₃ | 125–127 |
| H | CH₂CH₂F | H | CH₃ | OCH₃ | 132–134 |
| H | CH₂CH₂F | H | CH₃ | CH₃ | |
| H | CH₂CH₂F | H | Cl | OCH₃ | |
| H | CH₂CH₂F | H | Br | OCH₃ | |
| H | CH₂CH₂F | H | CH₃ | H | |
| H | CH₂CH₂F | H | OCH₃ | H | |
| H | CH₂CH₂F | H | OCH₃ | CH₂OC₂H₅ | |
| H | CH₂CH₂F | H | OCF₂H | OCH₃ | |
| H | CH₂CH₂F | H | OCH₃ | CH(OCH₃)₂ | |
| H | CH₂CH₂F | H | CH₃ | OC₂H₅ | |
| H | CH₂CH₂F | H | CH₃ | CH₂OCH₃ | |
| H | CH₂CH₂F | H | OCH₃ | CH₂OCH₃ | |
| H | CH₂CH₂F | H | OCH₃ | C₂H₅ | |
| H | CH₂CH₂F | H | OC₂H₅ | OCH₃ | |
| H | CH₂CH₂F | H | OCH₂CF₃ | OCH₃ | |
| H | CH₂CH₂F | H | CF₃ | OCH₃ | |
| H | CH₂CH₂F | H | CH₂F | OCH₃ | |
| H | CH₂CH₂F | H | CH₂Cl | OCH₃ | |
| H | CH₂CH₂F | H | CH₂Br | OCH₃ | |
| H | CH₂CH₂F | H | F | OCH₃ | |
| H | CH₂CH₂F | H | I | OCH₃ | |
| H | CH₂CH₂F | H | OCH₂CH₂F | OCH₃ | |
| H | CH₂CH₂F | H | OCH₂CH₂CF₃ | OCH₃ | |
| H | CH₂CH₂F | H | OCH₂CHF₂ | CH₃ | |
| H | CH₂CH₂F | H | OCH₂CF₃ | CH₃ | |
| H | CH₂CH₂F | H | Cl | OC₂H₅ | |
| H | CH₂CH₂F | H | OC₂H₅ | NHCH₃ | |
| H | CH₂CH₂F | H | OCH₃ | CH₂SCH₃ | |
| H | CH₂CH₂F | H | OCF₂H | CH₃ | |
| H | CH₂CH₂F | H | Cl | OCF₂H | |
| H | CH₂Cl | H | OCH₃ | OCH₃ | 108–110 |
| H | CH₂Cl | H | CH₃ | OCH₃ | |
| H | CH₂Cl | H | CH₃ | CH₃ | 124–125 |
| H | CH₂Cl | H | Cl | OCH₃ | |
| H | CH₂Cl | H | Br | OCH₃ | |
| H | CH₂Cl | H | CH₃ | H | |
| H | CH₂Cl | H | OCH₃ | H | |
| H | CH₂Cl | H | OCH₃ | CH₂OC₂H₅ | |
| H | CH₂Cl | H | OCF₂H | OCH₃ | |
| H | CH₂Cl | H | OCH₃ | CH(OCH₃)₂ | |
| H | CH₂Cl | H | CH₃ | OC₂H₅ | |
| H | CH₂Cl | H | CH₃ | CH₂OCH₃ | |
| H | CH₂Cl | H | OCH₃ | CH₂OCH₃ | |
| H | CH₂Cl | H | OCH₃ | C₂H₅ | |
| H | CH₂Cl | H | OC₂H₅ | OCH₃ | |
| H | CH₂Cl | H | OCH₂CF₃ | OCH₃ | |
| H | CH₂Cl | H | CF₃ | OCH₃ | |
| H | CH₂Cl | H | CH₂F | OCH₃ | |
| H | CH₂Cl | H | CH₂Cl | OCH₃ | |
| H | CH₂Cl | H | CH₂Br | OCH₃ | |
| H | CH₂Cl | H | F | OCH₃ | |
| H | CH₂Cl | H | I | OCH₃ | |

TABLE 1-continued

| R¹ | R² | R³ | X | Y | mp (°C.) |
|---|---|---|---|---|---|
| H | CH₂Cl | H | OCH₂CH₂F | OCH₃ | |
| H | CH₂Cl | H | OCH₂CH₂CF₃ | OCH₃ | |
| H | CH₂Cl | H | OCH₂CHF₂ | CH₃ | |
| H | CH₂Cl | H | OCH₂CF₃ | CH₃ | |
| H | CH₂Cl | H | Cl | OC₂H₅ | |
| H | CH₂Cl | H | OC₂H₅ | NHCH₃ | |
| H | CH₂Cl | H | OCH₃ | CH₂SCH₃ | |
| H | CH₂Cl | H | OCF₂H | CH₃ | |
| H | CH₂Cl | H | Cl | OCF₂H | |
| H | CHClCH₃ | H | OCH₃ | OCH₃ | |
| H | CHClCH₃ | H | CH₃ | OCH₃ | 137–139 |
| H | CHClCH₃ | H | CH₃ | CH₃ | 141–143 |
| H | CHClCH₃ | H | Cl | OCH₃ | |
| H | CHClCH₃ | H | Br | OCH₃ | |
| H | CHClCH₃ | H | CH₃ | H | |
| H | CHClCH₃ | H | OCH₃ | H | |
| H | CHClCH₃ | H | OCH₃ | CH₂OC₂H₅ | |
| H | CHClCH₃ | H | OCF₂H | OCH₃ | |
| H | CHClCH₃ | H | OCH₃ | CH(OCH₃)₂ | |
| H | CHClCH₃ | H | CH₃ | OC₂H₅ | |
| H | CHClCH₃ | H | CH₃ | CH₂OCH₃ | |
| H | CHClCH₃ | H | OCH₃ | CH₂OCH₃ | |
| H | CHClCH₃ | H | OCH₃ | C₂H₅ | |
| H | CHClCH₃ | H | OC₂H₅ | OCH₃ | |
| H | CHClCH₃ | H | OCH₂CF₃ | OCH₃ | |
| H | CHClCH₃ | H | CF₃ | OCH₃ | |
| H | CHClCH₃ | H | CH₂F | OCH₃ | |
| H | CHClCH₃ | H | CH₂Cl | OCH₃ | |
| H | CHClCH₃ | H | CH₂Br | OCH₃ | |
| H | CHClCH₃ | H | F | OCH₃ | |
| H | CHClCH₃ | H | I | OCH₃ | |
| H | CHClCH₃ | H | OCH₂CH₂F | OCH₃ | |
| H | CHClCH₃ | H | OCH₂CH₂CF₃ | OCH₃ | |
| H | CHClCH₃ | H | OCH₂CHF₂ | CH₃ | |
| H | CHClCH₃ | H | OCH₂CF₃ | CH₃ | |
| H | CHClCH₃ | H | Cl | OC₂H₅ | |
| H | CHClCH₃ | H | OC₂H₅ | NHCH₃ | |
| H | CHClCH₃ | H | OCH₃ | CH₂SCH₃ | |
| H | CHClCH₃ | H | OCF₂H | CH₃ | |
| H | CHClCH₃ | H | Cl | OCF₂H | |
| H | CH₂Br | H | OCH₃ | OCH₃ | |
| H | CH₂Br | H | CH₃ | OCH₃ | |
| H | CH₂Br | H | CH₃ | CH₃ | |
| H | CH₂Br | H | Cl | OCH₃ | |
| H | CH₂Br | H | Br | OCH₃ | |
| H | CH₂Br | H | CH₃ | H | |
| H | CH₂Br | H | OCH₃ | H | |
| H | CH₂Br | H | OCH₃ | CH₂OC₂H₅ | |
| H | CH₂Br | H | OCF₂H | OCH₃ | |
| H | CH₂Br | H | OCH₃ | CH(OCH₃)₂ | |
| H | CH₂Br | H | CH₃ | OC₂H₅ | |
| H | CH₂Br | H | CH₃ | CH₂OCH₃ | |
| H | CH₂Br | H | OCH₃ | CH₂OCH₃ | |
| H | CH₂Br | H | OCH₃ | C₂H₅ | |
| H | CH₂Br | H | OCH₂CF₃ | OCH₃ | |
| H | CH₂Br | H | OC₂H₅ | OCH₃ | |
| H | CH₂Br | H | CF₃ | OCH₃ | |
| H | CH₂Br | H | CH₂F | OCH₃ | |
| H | CH₂Br | H | CH₂Cl | OCH₃ | |
| H | CH₂Br | H | CH₂Br | OCH₃ | |
| H | CH₂Br | H | F | OCH₃ | |
| H | CH₂Br | H | I | OCH₃ | |
| H | CH₂Br | H | OCH₂CH₂F | OCH₃ | |
| H | CH₂Br | H | OCH₂CH₂CF₃ | OCH₃ | |
| H | CH₂Br | H | OCH₂CHF₂ | CH₃ | |
| H | CH₂Br | H | OCH₂CF₃ | CH₃ | |

TABLE 1-continued

| R¹ | R² | R³ | X | Y | mp (°C.) |
|---|---|---|---|---|---|
| H | CH$_2$Br | H | Cl | OC$_2$H$_5$ | |
| H | CH$_2$Br | H | OC$_2$H$_5$ | NHCH$_3$ | |
| H | CH$_2$Br | H | OCH$_3$ | CH$_2$SCH$_3$ | |
| H | CH$_2$Br | H | OCF$_2$H | CH$_3$ | |
| H | CH$_2$Br | H | Cl | OCF$_2$H | |
| H | CHF$_2$ | H | OCH$_3$ | OCH$_3$ | 184–186 |
| H | CHF$_2$ | H | CH$_3$ | OCH$_3$ | 166–167 |
| H | CHF$_2$ | H | CH$_3$ | CH$_3$ | |
| H | CHF$_2$ | H | Cl | OCH$_3$ | |
| H | CHF$_2$ | H | Br | OCH$_3$ | |
| H | CHF$_2$ | H | CH$_3$ | H | |
| H | CHF$_2$ | H | OCH$_3$ | H | |
| H | CHF$_2$ | H | OCH$_3$ | CH$_2$OC$_2$H$_5$ | |
| H | CHF$_2$ | H | OCF$_2$H | OCH$_3$ | |
| H | CHF$_2$ | H | OCH$_3$ | CH(OCH$_3$)$_2$ | |
| H | CHF$_2$ | H | CH$_3$ | OC$_2$H$_5$ | |
| H | CHF$_2$ | H | CH$_3$ | CH$_2$OCH$_3$ | |
| H | CHF$_2$ | H | OCH$_3$ | CH$_2$OCH$_3$ | |
| H | CHF$_2$ | H | OCH$_3$ | C$_2$H$_5$ | |
| H | CHF$_2$ | H | OC$_2$H$_5$ | OCH$_3$ | |
| H | CHF$_2$ | H | OCH$_2$CF$_3$ | OCH$_3$ | |
| H | CHF$_2$ | H | CF$_3$ | OCH$_3$ | |
| H | CHF$_2$ | H | CH$_2$F | OCH$_3$ | |
| H | CHF$_2$ | H | CH$_2$Cl | OCH$_3$ | |
| H | CHF$_2$ | H | CH$_2$Br | OCH$_3$ | |
| H | CHF$_2$ | H | F | OCH$_3$ | |
| H | CHF$_2$ | H | I | OCH$_3$ | |
| H | CHF$_2$ | H | OCH$_2$CH$_2$F | OCH$_3$ | |
| H | CHF$_2$ | H | OCH$_2$CH$_2$CF$_3$ | OCH$_3$ | |
| H | CHF$_2$ | H | OCH$_2$CHF$_2$ | CH$_3$ | |
| H | CHF$_2$ | H | OCH$_2$CF$_3$ | CH$_3$ | |
| H | CHF$_2$ | H | Cl | OC$_2$H$_5$ | |
| H | CHF$_2$ | H | OC$_2$H$_5$ | NHCH$_3$ | |
| H | CHF$_2$ | H | OCH$_3$ | CH$_2$SCH$_3$ | |
| H | CHF$_2$ | H | OCF$_2$H | CH$_3$ | |
| H | CHF$_2$ | H | Cl | OCF$_2$H | |
| H | CHFCl | H | OCH$_3$ | OCH$_3$ | |
| H | CHFCl | H | CH$_3$ | OCH$_3$ | |
| H | CHFCl | H | CH$_3$ | CH$_3$ | |
| H | CHFCl | H | Cl | OCH$_3$ | |
| H | CHFCl | H | Br | OCH$_3$ | |
| H | CHFCl | H | CH$_3$ | H | |
| H | CHFCl | H | OCH$_3$ | H | |
| H | CHFCl | H | OCH$_3$ | CH$_2$OC$_2$H$_5$ | |
| H | CHFCl | H | OCF$_2$H | OCH$_3$ | |
| H | CHFCl | H | OCH$_3$ | CH(OCH$_3$)$_2$ | |
| H | CHFCl | H | CH$_3$ | OC$_2$H$_5$ | |
| H | CHFCl | H | CH$_3$ | CH$_2$OCH$_3$ | |
| H | CHFCl | H | OCH$_3$ | CH$_2$OCH$_3$ | |
| H | CHFCl | H | OCH$_3$ | C$_2$H$_5$ | |
| H | CHFCl | H | OCH$_2$CF$_3$ | OCH$_3$ | |
| H | CHFCl | H | OC$_2$H$_5$ | OCH$_3$ | |
| H | CHFCl | H | CF$_3$ | OCH$_3$ | |
| H | CHFCl | H | CH$_2$F | OCH$_3$ | |
| H | CHFCl | H | CH$_2$Cl | OCH$_3$ | |
| H | CHFCl | H | CH$_2$Br | OCH$_3$ | |
| H | CHFCl | H | F | OCH$_3$ | |
| H | CHFCl | H | I | OCH$_3$ | |
| H | CHFCl | H | OCH$_2$CH$_2$F | OCH$_3$ | |
| H | CHFCl | H | OCH$_2$CH$_2$CF$_3$ | OCH$_3$ | |
| H | CHFCl | H | OCH$_2$CHF$_2$ | CH$_3$ | |
| H | CHFCl | H | OCH$_2$CF$_3$ | CH$_3$ | |
| H | CHFCl | H | Cl | OC$_2$H$_5$ | |
| H | CHFCl | H | OC$_2$H$_5$ | NHCH$_3$ | |
| H | CHFCl | H | OCH$_3$ | CH$_2$SCH$_3$ | |
| H | CHFCl | H | OCF$_2$H | CH$_3$ | |

TABLE 1-continued

Structure: R¹-substituted phenyl with CH(OH)R² group and -SO₂NH-C(=O)-N(R₃)- linked to pyrimidine bearing X and Y substituents.

| R¹ | R² | R³ | X | Y | mp (°C.) |
|---|---|---|---|---|---|
| H | CHFCl | H | Cl | OCF₂H | |
| H | CHFCl | H | n-C₃H₇ | OCH₃ | |
| H | CHFCl | H | OCH₃ | NHCH₃ | |
| H | CHFCl | H | OCH₃ | N(CH₃)₂ | |
| H | CHFCl | H | OCH₃ | cyclopropyl | |
| H | CHFCl | H | OCH₃ | OCH₂CH₂OCH₃ | |
| H | CHFCl | H | OC₂H₅ | CH₂SCH₃ | |
| H | CHFCl | H | OCH₃ | CH(SCH₃)OC₂H₅ | |
| H | CHFCl | H | OCH₃ | CH(SC₂H₅)₂ | |
| H | CHFCl | H | OCH₃ | 1,3-dioxolan-2-yl | |
| H | CHFCl | H | OCH₃ | N(OCH₃)(CH₃) | |
| H | CHFCl | H | OCH₃ | C₂H₅ | |
| H | CHFCl | H | OCH₃ | CF₃ | |
| 5-F | CH₂F | H | OCH₃ | OCH₃ | |
| 6-Cl | CH₂F | H | OCH₃ | OCH₃ | |
| 6-Cl | CH₂Cl | H | OCH₃ | OCH₃ | |
| 6-Cl | CH₂F | H | CH₃ | OCH₃ | |
| 6-Cl | CH₂F | H | CH₃ | CH₃ | |
| 6-Cl | CH₂F | H | Cl | OCH₃ | |
| 5-Br | CH₂F | H | OCH₃ | OCH₃ | |
| 5-CH₂CN | CH₂F | H | OCH₃ | OCH₃ | |
| 5-OCH₃ | CH₂F | H | OCH₃ | OCH₃ | |
| 5-SCH₃ | CH₂F | H | OCH₃ | OCH₃ | |
| 5-OCF₂H | CH₂F | H | OCH₃ | OCH₃ | |
| H | CH₂F | CH₃ | OCH₃ | OCH₃ | |
| H | CH₂F | CH₃ | CH₃ | OCH₃ | |
| H | CH₂Cl | CH₃ | OCH₃ | OCH₃ | |
| H | CHF₂ | CH₃ | OCH₃ | OCH₃ | |
| H | CH₂Br | CH₃ | OCH₃ | OCH₃ | |
| 6-Cl | CH₂Cl | CH₃ | OCH₃ | OCH₃ | |

TABLE 2

Structure: R¹-substituted phenyl with CH(OH)R² group and -SO₂NH-C(=O)-N(R₃)- linked to pyrimidine bearing X and Y substituents.

| R¹ | R² | R³ | X | Y | mp (°C.) |
|---|---|---|---|---|---|
| H | CH₂F | H | CH₃ | OCH₃ | |
| H | CH₂F | H | OCH₃ | OCH₃ | 119–122 |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |

TABLE 2-continued

| R¹ | R² | R³ | X | Y | mp (°C.) |
|---|---|---|---|---|---|
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | N(CH₃)₂ | |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCl | H | C₂H₅ | OCH₃ | |
| 5-F | CH₂F | H | CH₃ | OCH₃ | |
| 6-Cl | CH₂F | H | OCH₃ | CH₃ | |
| 5-Br | CH₂F | H | CH₃ | OCH₃ | |
| 5-CH₂CN | CH₂F | H | OCH₃ | OCH₃ | |
| 5-OCH₃ | CH₂F | H | CH₃ | OCH₃ | |
| 5-SCH₃ | CH₂F | H | CH₃ | OCH₃ | |
| 5-OCF₂H | CH₂F | H | CH₃ | OCH₃ | |
| 6-Cl | CH₂Cl | H | CH₃ | OCH₃ | |
| 6-Cl | CH₂Br | H | OCH₃ | OCH₃ | |
| 6-Cl | CH₂F | H | OC₂H₅ | NHCH₃ | |
| 6-Cl | CH₂F | H | OCH₃ | OCH₃ | |

TABLE 3

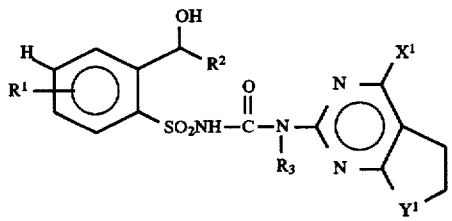

| R¹ | R² | R³ | X¹ | Y¹ | mp (°C.) |
|---|---|---|---|---|---|
| H | $CH_2F$ | H | $CH_3$ | O | |
| H | $CH_2F$ | H | $OCH_3$ | O | |
| H | $CH_2F$ | H | $OC_2H_5$ | O | |
| H | $CH_2F$ | H | $OCF_2H$ | O | |
| H | $CH_2F$ | H | $OCH_3$ | $CH_2$ | |
| H | $CH_2Cl$ | H | $CH_3$ | O | |
| H | $CH_2Cl$ | H | $OCH_3$ | O | |
| H | $CH_2Br$ | H | $CH_3$ | O | |
| H | $CHFCH_3$ | H | $CH_3$ | O | |
| H | $CHClCH_3$ | H | $CH_3$ | O | |
| 5-$OCH_3$ | $CH_2F$ | H | $CH_3$ | O | |
| 6-Cl | $CH_2F$ | H | $CH_3$ | O | |
| 3-$CH_3$ | $CH_2F$ | H | $CH_3$ | O | |
| 5-$CH_2CN$ | $CH_2F$ | H | $CH_3$ | O | |
| H | $CH_2F$ | $CH_3$ | $CH_3$ | O | |
| H | $CHF_2$ | H | $OCH_3$ | O | |

TABLE 4

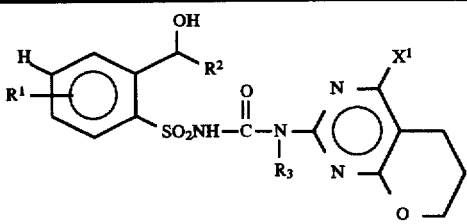

| R¹ | R² | R³ | X¹ | mp (°C.) |
|---|---|---|---|---|
| H | $CH_2F$ | H | $CH_3$ | |
| H | $CH_2F$ | H | $OCH_3$ | |
| H | $CH_2F$ | H | $OC_2H_5$ | |
| H | $CH_2F$ | H | $OCF_2H$ | |
| H | $CH_2Cl$ | H | $CH_3$ | |
| H | $CH_2Cl$ | H | $OCH_3$ | |
| H | $CH_2Br$ | H | $CH_3$ | |
| H | $CHF_2$ | H | $CH_3$ | |
| H | $CHF_2$ | H | $OCH_3$ | |
| H | $CHFCH_3$ | H | $CH_3$ | |
| H | $CHFCH_3$ | H | $OCH_3$ | |
| H | $CHFCl$ | H | $OCH_3$ | |
| H | $CHFCl$ | H | $CH_3$ | |
| 6-Cl | $CHFCl$ | H | $CH_3$ | |
| 6-Cl | $CHFCl$ | H | $OCH_3$ | |
| 6-Cl | $CH_2F$ | H | $CH_3$ | |
| 6-Cl | $CH_2F$ | H | $OCH_3$ | |
| 5-$CH_2CN$ | $CH_2F$ | H | $CH_3$ | |
| 5-$OCH_3$ | $CH_2F$ | H | $CH_3$ | |
| H | $CH_2F$ | $CH_3$ | $CH_3$ | |
| H | $CH_2F$ | $CH_3$ | $OCH_3$ | |
| H | $CHClCH_3$ | H | $OCH_3$ | |
| H | $CH_2CH_2F$ | H | $OCH_3$ | |

TABLE 5

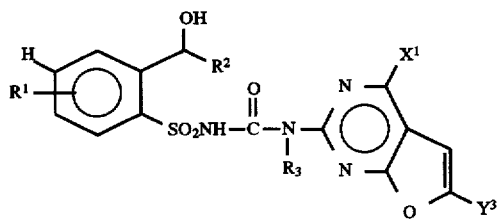

| R¹ | R² | R³ | X¹ | Y³ | mp (°C.) |
|---|---|---|---|---|---|
| H | $CH_2F$ | H | $CH_3$ | $CH_3$ | |
| H | $CH_2F$ | H | $OCH_3$ | $CH_3$ | |
| H | $CH_2F$ | H | $OC_2H_5$ | $CH_3$ | |
| H | $CH_2F$ | H | $OCF_2H$ | $CH_3$ | |
| H | $CH_2F$ | H | $OCH_3$ | H | |
| H | $CH_2F$ | H | $CH_3$ | H | |
| H | $CH_2Cl$ | H | $OCH_3$ | $OCH_3$ | |
| H | $CHFCl$ | H | $OCH_3$ | $OCH_3$ | |
| H | $CHFCl$ | H | $OCH_3$ | $CH_3$ | |
| H | $CHFCH_3$ | H | $OCH_3$ | $OCH_3$ | |
| H | $CHF_2$ | H | $OCH_3$ | $OCH_3$ | |
| 6-F | $CH_2F$ | H | $OCH_3$ | $OCH_3$ | |
| 5-$OCH_3$ | $CH_2F$ | H | $OCH_3$ | $OCH_3$ | |
| 6-Cl | $CH_2F$ | H | $OCH_3$ | $OCH_3$ | |
| 3-$CH_3$ | $CH_2F$ | H | $OCH_3$ | $OCH_3$ | |
| 5-$CH_2CN$ | $CH_2F$ | H | $OCH_3$ | $CH_3$ | |
| H | $CH_2Cl$ | H | $OCH_3$ | $CH_3$ | |
| H | $CH_2Br$ | H | $OCH_3$ | $CH_3$ | |
| H | $CH_2CH_2F$ | H | $OCH_3$ | $CH_3$ | |
| H | $CHClCH_3$ | H | $OCH_3$ | $CH_3$ | |
| H | $CHF_2$ | H | $OCH_3$ | $CH_3$ | |
| 6-Cl | $CH_2F$ | H | $OCH_3$ | $CH_3$ | |

TABLE 6

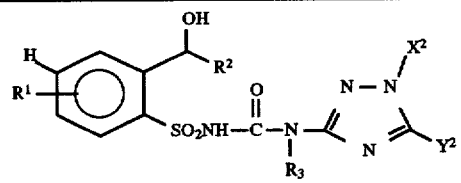

| R¹ | R² | R³ | X² | Y² | mp (°C.) |
|---|---|---|---|---|---|
| H | $CH_2F$ | H | $CH_3$ | $OCH_3$ | |
| H | $CH_2F$ | H | $CH_3$ | $OC_2H_5$ | |
| H | $CH_2F$ | H | $CH_3$ | $SCH_3$ | |
| H | $CH_2F$ | H | $CH_3$ | $SC_2H_5$ | |
| H | $CH_2F$ | H | $CH_3$ | $CH_3$ | |
| H | $CH_2F$ | H | $CH_3$ | $C_2H_5$ | |
| H | $CH_2F$ | H | $C_2H_5$ | $OCH_3$ | |
| H | $CH_2F$ | H | $CH_2CF_3$ | | |
| H | $CH_2Cl$ | H | $CH_3$ | $OCH_3$ | |
| H | $CHFCl$ | H | $CH_3$ | $OCH_3$ | |
| H | $CHF_2$ | H | $CH_3$ | $OCH_3$ | |
| 3-$CH_3$ | $CH_2F$ | H | $CH_3$ | $OCH_3$ | |
| 6-F | $CH_2F$ | H | $CH_3$ | $OCH_3$ | |
| 6-Cl | $CH_2F$ | H | $CH_3$ | $OCH_3$ | |
| 5-$OCH_3$ | $CH_2F$ | H | $CH_3$ | $OCH_3$ | |
| 6-Cl | $CH_2F$ | H | $CH_3$ | $CH_3$ | |
| 5-$CH_2CN$ | $CH_2F$ | H | $CH_3$ | $OCH_3$ | |
| H | $CH_2Br$ | H | $CH_3$ | $OCH_3$ | |
| H | $CH_2CH_2F$ | H | $CH_3$ | $OCH_3$ | |
| H | $CHFCl$ | H | $CH_3$ | $CH_3$ | |
| H | $CHFCH_3$ | H | $CH_3$ | $OCH_3$ | |
| H | $CHClCH_3$ | H | $CH_3$ | $OCH_3$ | |

TABLE 7

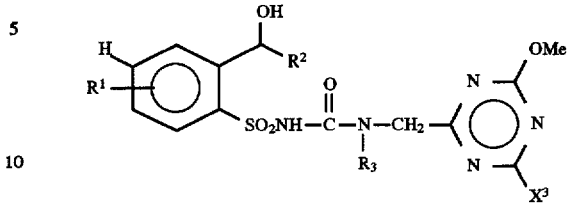

| R¹ | R² | R³ | X³ | mp (°C.) |
|---|---|---|---|---|
| H | $CH_2F$ | H | $CH_3$ | |
| H | $CH_2F$ | H | $OCH_3$ | |
| H | $CH_2Cl$ | H | $CH_3$ | |
| H | $CH_2Cl$ | H | $OCH_3$ | |
| H | $CHF_2$ | H | $OCH_3$ | |
| H | $CHF_2$ | H | $CH_3$ | |
| H | CHFCl | H | $CH_3$ | |
| H | CHFCl | H | $OCH_3$ | |
| H | $CHFCH_3$ | H | $CH_3$ | |
| H | $CHFCH_3$ | H | $OCH_3$ | |
| H | $CHClCH_3$ | H | $OCH_3$ | |
| 6-F | $CH_2F$ | H | $OCH_3$ | |
| 6-Cl | $CH_2F$ | H | $OCH_3$ | |
| 3-$CH_3$ | $CH_2F$ | H | $CH_3$ | |
| 5-$OCH_3$ | $CH_2F$ | H | $CH_3$ | |
| 5-$CH_2CN$ | $CH_2F$ | H | $CH_3$ | |

TABLE 7-continued

| R¹ | R² | R³ | X³ | mp (°C.) |
|---|---|---|---|---|
| 6-Cl | $CH_2F$ | H | $OCH_3$ | |
| H | $CH_2CH_2F$ | H | $OCH_3$ | |
| H | $CH_2F$ | $CH_3$ | $OCH_3$ | |
| H | $CH_2CH_2F$ | H | $CH_3$ | |

TABLE 8

| R¹ | R² | R³ | X⁴ | Y⁴ | Z¹ | mp |
|---|---|---|---|---|---|---|
| H | $CH_2F$ | H | $CH_3$ | $CH_3$ | CH | |
| H | $CH_2F$ | H | $CH_3$ | $CH_3$ | N | |
| H | $CH_2F$ | H | $OCH_3$ | $CH_3$ | CH | |
| H | $CH_2F$ | H | $OCH_3$ | $CH_3$ | N | |
| H | $CH_2F$ | H | $OCH_3$ | $OCH_3$ | CH | |
| H | $CH_2F$ | H | $OCH_3$ | $OCH_3$ | N | |
| H | $CH_2F$ | H | Cl | $CH_3$ | CH | |
| H | $CH_2F$ | H | $OCH_3$ | Cl | CH | |
| H | $CH_2F$ | H | $OC_2H_5$ | $CH_3$ | CH | |
| H | $CH_2F$ | H | $CH_2OCH_3$ | $CH_3$ | N | |
| H | $CH_2F$ | H | $CH_2OCH_3$ | $OCH_3$ | CH | |
| H | $CH_2F$ | H | $OC_2H_5$ | $OC_2H_5$ | N | |
| H | $CH_2Cl$ | H | $OCH_3$ | $CH_3$ | CH | |
| H | $CH_2Cl$ | H | $OCH_3$ | $OCH_3$ | CH | |
| H | $CH_2Cl$ | H | $OCH_3$ | $CH_3$ | N | |
| H | $CH_2Cl$ | H | $OCH_3$ | $OCH_3$ | N | |
| H | $CHF_2$ | H | $OCH_3$ | $CH_3$ | CH | |
| H | CHFCl | H | $OCH_3$ | $CH_3$ | CH | |
| H | $CHFCH_3$ | H | $OCH_3$ | $CH_3$ | CH | |
| H | $CHClCH_3$ | H | $OCH_3$ | $CH_3$ | CH | |
| 6-F | $CH_2F$ | H | $OCH_3$ | $CH_3$ | CH | |
| 3-$CH_3$ | $CH_2F$ | H | $OCH_3$ | $CH_3$ | CH | |
| 5-$OCH_3$ | $CH_2F$ | H | $OCH_3$ | $CH_3$ | CH | |
| 6-Cl | $CH_2F$ | H | $OCH_3$ | $CH_3$ | CH | |
| 5-$CH_2CN$ | $CH_2F$ | H | $OCH_3$ | $CH_3$ | CH | |
| H | $CH_2F$ | $CH_3$ | $OCH_3$ | $CH_3$ | CH | |
| H | $CH_2CH_2F$ | H | $OCH_3$ | $CH_3$ | CH | |
| H | $CH_2CH_2Cl$ | H | $OCH_3$ | $CH_3$ | CH | |
| H | CHFCl | H | $OCH_3$ | $OCH_3$ | CH | |

TABLE 9

Structure: benzene ring with OH, H, R¹, R², and SO₂NH—C(=W)—N(R₃)— linked to a heterocyclic ring with N, X, Y, Z¹

| R¹ | R² | R³ | W | X | Y | Z¹ |
|---|---|---|---|---|---|---|
| H | CH₂F | H | S | OCH₃ | OCH₃ | CH |
| H | CH₂F | H | S | CH₃ | OCH₃ | N |
| H | CH₂F | H | S | OCH₃ | OCH₃ | N |
| H | CH₂Cl | H | S | OCH₃ | OCH₃ | CH |
| H | CH₂Br | H | S | OCH₃ | OCH₃ | CH |
| H | CHF₂ | H | S | OCH₃ | OCH₃ | CH |
| H | CHFCl | H | S | OCH₃ | OCH₃ | CH |
| H | CHFCH₃ | H | S | OCH₃ | OCH₃ | CH |
| H | CHClCH₃ | H | S | OCH₃ | OCH₃ | CH |
| 5-OCH₃ | CH₂F | H | S | OCH₃ | OCH₃ | CH |
| 6-Cl | CH₂F | H | S | OCH₃ | OCH₃ | CH |
| H | CH₂F | CH₃ | S | OCH₃ | OCH₃ | CH |
| H | CH₂F | H | S | OCH₃ | CH₃ | CH |

Test results indicate that the compounds of the present invention are highly active pro-emergent or post-emergent herbicides or plant growth regulants. Many of them have utility for broad-spectrum pre- and/or post-emergency weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat and barley. Alternatively, the subject compounds are useful to modify, plant growth.

The rates of application for the compounds of the present invention are determined by a number of factors, including their use as plant growth modifiers or as herbicides, the crop species involved, the types of weeds to be controlled, weather and climate, formulations selected, mode of application, amount of foliage present, etc.

In general terms, the subject compounds should be applied at levels of around 0.05 to 10 kg/ha, the lower rates being suggested for use on lighter soils and/or those having a low organic matter content, for plant growth modifications or for situations where only short-term persistence is required.

Formulations

Useful formulations of the compounds of formula(I) can be prepared in conventional ways. They include dusts, granules, pellets, solutions, suspensions, emulsions, wettable powders, emulsifiable concentrates and the like. Many of these may be applied directly.

Sprayable formulations can be extented in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (1) about 0.1% to 20% surfactant(s) and (2) about 1% to 99.9% solid or liquid inert diluent(s). More specially, they will contain these ingredients in the following approximate proportions:

| Formulations | Active Ingredient | Diluent(s) | Surfactant(s) |
|---|---|---|---|
| Wettable Powders | 20–90 | 0–74 | 1–10 |
| Oil Suspensions, Emulsions, Solutions (including Emulsifiable concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a surfactant or a diluent equals 100 weight percent.

Lower or higher levels of active ingredient can, of course, be present depending on the intended use and the physical properties of the compound. Higher ratios of surfactants to activate ingredient are sometimes desirable, and are achieved by incorporation into the formation or by tank mixing.

Typical solid diluents are described in Watkins, et al., "Handbook of Insecticide Dust Diluents and Carriers", 2nd Ed., Dorland Books, Caldwell, N.J., but other solids, either mined or monufactured, may be used. The more absorptive diluents are preferred for wettable powders and the denser ones for dusts.

Typical liquid diluents and solvents are described in Marsden, "Solvent Guide", 2nd Ed., Interscience, New York, 1950. Solubility under 0.1% is preferred for suspension concentrates; Solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses.

All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques.

See J. E. Browning, "Agglomeration", Chemical Engineering, Dec. 4, 1967, pp, 147ff. and "Perry's chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41; R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182; H. Gysin and E. Knusli, U.S. Pat. No. 2,891,855, Jun. 23, 1959, Col. 3, line 66 through Col. 5, line 17 and Examples 1–4; G. C. Klingman, "Weed Control as a Science", John Wiley and S. A. Evans, "Weed control Handbook", 5th Ed., Blackwell Scientific Publications, Oxford, 1968, pp. 101–103.

The compounds of the present invention can be used independently and may be used in combination with any other commercial herbicide. A summary of the possible combination herbicides is given below

| Common Name | | |
|---|---|---|
| acetochlor | acifluorfen | AC 252,214 |
| AC 263,499 | acrolein | alachlor |
| ametryn | amitrole | AMS |
| asulam | assure | atrazine |
| BAS-514 | barban | benefin |
| bensulfuron methyl | bensulide | bentazon |
| benzofluor | benzoylprop | bifenox |
| bromacil | bromoxynil | butachlor |
| buthidazole | butralin | butylate |
| cacodylic acid | CDAA | CDEC |
| CGA 82725 | CH-83 | chloramben |
| chlorbromuron | chlorimuron ethyl | chloroxuron |
| chlorpropham | chlorsulfuron | chlortoluron |
| cinmethylin | clethodim | clomazone |
| cloproxydim | clopyralid | CMA |
| cyanzine | cycloate | cycluron |
| cyperquat | cyprazine | cyprazole |
| cypromid | dalapon | dazomet |
| DCPA | desmediphan | desmetryn |
| diallate | dicamba | dichlorbenil |
| dichlorprop | dichlofop | diethatyl |
| difenzoquat | dinitramine | dinoseb |
| diphenamid | dipropetryn | diquat |
| diuron | DNOC | DOWCO453ME |
| DPX-M6316 | DSMA | endothall |
| EPTC | ethalfluralin | ethoxfumesate |
| Express | fenac | fenoxaprop ethyl |
| fenuron | fenuron TCA | flamprop |
| fluazifop | fluazifop-butyl | fluazifop-P |
| fluchloralin | fluometuron | fluorochloridone |
| fluorodifen | fluoroglycofen | fluridone |
| fomesafen | fosamine | glyphosate |
| haloxyfop | harmoney | hexaflurate |
| hexazinone | HW-52 | imazamethabenz |
| imazapyr | imazaquin | imazethapyr |
| ioxynil | isopropalin | isoproturon |
| isouron | isoxaben | karbutilate |
| lactofen | lenacil | linuron |
| MAA | MAMA | MCPA |
| MCPB | mecoprop | mefluidide |
| methalpropalin | methabenzthiazuron | metham |
| methazole | methoxuron | metolachlor |
| metribuzin | metsulfuron methyl | MH |
| molinate | monolinuron | monuron |
| monuron TCA | MSMA | My-93 |
| napropamide | naproanilide | naptalam |
| neburon | nitralin | nitrofen |
| nitrofluorfen | norea | norfluazon |
| NTN-801 | oryzalin | oxadiazon |
| oxyfluorfen | paraquat | pebulate |
| pendimethalin | perfluidone | phenmedipham |
| picloram | PPG-1013 | pretilachlor |
| procyazine | profluralin | prometon |
| prometryn | pronamide | propachlor |
| propanil | propazine | propham |
| prosulfalin | prynachlor | pyrazon |
| pyrazolate | quizalofop ethyl | quizalofop |
| SC-2957 | secbumeton | sethoxydim |
| siduron | simazine | SL-49 |
| sulfometuron methyl | TCA | tebuthiuron |
| terbacil | terbuchlor | terbuthylazine |
| terbutol | terbutryn | thiameturon methyl |
| thiobencarb | triallate | triclopyr |
| tridiphane | trifluralin | trimeturon |
| 2,4-D | 2,4-DB | vernolate |
| X-52 | xylachlor | |

EXAMPLE 1

N-t-butyl 2-(fluoroacetyl)benzenesulfonamide

N-t-butyl benzenesulfonamide (10 g, 0.047 mol) was dissolved in 100 ml of anhydrous tetrahydrofuran and the solution was cooled to 0° C. under nitrogen atmosphere, and herein 37.6 ml of 2.5N n-butyl lithium was added dropwise.

The solution stirred for 2.5 hr at room temperature was cooled to −78° C., and ethyl fluoracetate (5 ml, 0.052 mol) was added dropwise.

After slowly raising the reaction temperature, the reaction mixture was stirred for 12 hr at room temperature, and 5% hydrochloric acid and 50 ml of ethyl acetate were added and stirred to separate organic layer.

After extracting the water layer with ethylacetate, the combined organic layer was dried with magnesium sulfate, filtered and concentrated.

The obtained residue was chromatographed through silica gel using 1:3 of ethyl acetate-hexane as eluant to afford 5.3 g of the desired product (white solid, yield: 41%).

M.P.: 126° C.

$^1$H NMR (CDCl$_3$): δ 1.26(s, 9H), 4.96(s, 1H), 5.16(br s, 1H), 5.73(s, 1H), 7.40–7.80(m, 3H), 7.93–8.20(m, 1H).

IR (KBr) ν (NH) 3250 cm$^{-1}$, ν (C=O) 1700 cm$^{-1}$

EXAMPLE 2

2-(1-acetoxy-2-fluoroethyl)-N-t-butylbenzenesulfonamide

N-t-butyl 2-(fluoroacetyl)benzenesulfonamide (5 g, 0.018 mol) was dissolved in 100 ml of methanol, and sodium borohydride (0.7 g, 0.018 mol) was added potionwise in the solution.

After stirring for 30 min at 40° C., methanol was evaporated, and then the obtained residue was dissolved in methylene chloride and washed with 5% hydrochloric acid. The separated organic layer was dried, filtered and concentrated to obtain a residue of oil type.

The residue was dissolved in 100 ml of methylene chloride and acetic anhydride (1.98 ml, 0.02 mol), pyridine(1.6 ml, 0.02 mol) and N,N-dimethylaminopyridine (0.12 g, 0.001 mol) were added.

After stirring for 24 hr at room temperature, the solution was washed with 5% hydrochloric acid, and then the organic layer was dried with magnesium sulfate, filtered and concentrated.

The obtained residue was chromatographed through silica gel using 1:3 solution of ethyl acetate-hexane to afford 5.24 g of the desired product (white solid, yield: 92%).

M.P.: 118°–119° C.

$^1$H NMR (CDCl$_3$): δ 1.23(s, 9H), 2.20(s, 3H), 4.20–4.40 (m, 1H), 5.00–5.20(m, 1H), 5.70(br s, 1H), 6.50–7.10(m, 1H), 7.31–7.86(m, 3H), 8.06–8.36(m, 1H).

IR (KBr) ν (NH) 3250 cm$^{-1}$, ν (C=O) 1720 cm$^{-1}$

EXAMPLE 3

2-(1-acetoxy-2-fluoroethyl)benzenesulfonamide

N-t-butyl 2-(1-acetoxy-2-fluoroethyl) benzenesulfonamide (5.24 g, 0.016 mol) was dissolved in 2 ml of trifluoro acetic acid, and stirred at room temperature for 12 hr.

After concentrating the reacted solution under the reduced pressure, the obtained residue was dissolved in methylene chloride, and then the solution was washed one time with 5% sodium bicarbonate solution. The obtained organic layer was dried with magnesium sulfate, filtered and concentrated.

The residue was treated with ethylacetate and hexane and crystalized to afford 3 g of the desired product (white solid, yield: 71%).

M.P.: 122°–124° C.

¹H NMR (CDCl): δ 2.16(s, 3H), 4.20–4.40(m, 1H), 5.00–5.20(m, 1H), 5.70(br s, 2H), 6.46–7.00(m, 1H), 7.60–7.83(m, 3H), 8.06–8.33(m, 1H).

IR (KBr) ν (NH$_2$) 3250 cm$^{-1}$, 3350 cm$^{-1}$, ν (C=O) 1705 cm$^{-1}$

EXAMPLE 4

2-(1-acetoxy-2-fluoroethyl)-N-[(4,6-dimethoxypyrimidin-2-yl)aminocarbonyl] benzenesulfonamide 2-(1-acetoxy-2-fluoroethyl)benzenesulfonamide (1.91 g, 0.007 mol) was dissolved in 30 ml of acetonitrile, and herein phenyl(4,6-dimethoxypyrimidin-2-yl)carbamate (2 g, 0.007 mol) was added at room temperature.

After adding dropwise 0.9 ml of DBU, the solution was stirred for 30 min, diluted with 100 ml of methylene chloride, and acidified with 5% hydrochloric acid.

The obtained organic layer was washed one time with water, and dried with magnesium sulfate, filtered and concentrated.

The residue was crystalized with solution of ethylacetate/hexane/ethylether to afford 2.4 g of the desired product (white solid, yield: 80%)

M.P.: 176°–178° C.

¹H NMR (CDCl$_3$): δ 2.03(s, 3H), 3.93(s, 6H), 4.16–4.36 (m, 1H), 4.90–5.10(m, 1H), 5.76(s, 1H), 6.40–6.95(m, 1H), 7.30–7.70(m, 4H), 8.15–8.40(m, 1H), 13.2(br s, 1H).

IR (KBr) ν (C=O) 1740 cm$^{-1}$, 1700 cm$^{-1}$

EXAMPLE 5

N-[(4,6-dimethoxypyrimidin-2-yl)aminocarbonyl]-2-(1-hydroxy-2-fluoroethyl)benzenesulfonamide N-[(4,6-dimethoxy pyrimidin-2-yl)amino carbonyl]-2-(1-acetoxy-2-fluoroethyl)benzenesulfonamide (2.4 g, 0.005 mol) was dissolved in 80 ml of tetrahydrofuran, and herein lithium hydroxide monohydrate (0.7 g, 0.015 mol) and water were added.

After stirring for 12 hr at room temperature, the solution was diluted with 100 ml of water, and then conc-HCl was added dropwise at 0° C. to acidify the solution. The organic layer was obtained by adding 200 ml of methylene chloride, and the water layer was extracted two times with 100 ml of methylene chloride.

The combined organic layer was dried with magnesium sulfate, filtered and concentrated to obtain white solid.

This was washed with water and dried to afford 2.0 g of the desired product (white solid, yield: 93%)

M.P.: 171°–173° C.

¹H NMR (Acetone-d$_6$): δ 3.98(s, 6H), 4.29–4.67(m, 2H), 5.88(s, 1H), 5.98( m, 1H), 4.22–8.19(m, 4H), 9.48(s, 1H), 5.25(s, 1H), 13.0(s, 1H).

IR (KBr) ν (C=O) 1700 cm$^{-1}$

EXAMPLE 6

2-(1-acetoxy-2-fluoroethyl)-N-[(4-methoxy-6-methylpyrimidin-2-yl)aminocarbonyl] benzenesulfonamide 2-(1-acetoxy-2-fluoroethyl)benzenesulfonamide (1.09 g, 0.004 mol) was dissolved in 20 ml of acetonitrile, and herein phenyl(4-methoxy-6-methylpyrimidin-2-yl)carbamate (1.06 g, 0.004 mol) was added at room temperature.

After adding dropwise 0.6 ml of DBU, the solution was stirred for 30 min, diluted with 80 ml of methylene chloride, and acidified with 5% hydrochloric acid.

The obtained organic layer was washed with water, and concentrated the residue was chlomatographed with solvent of ethyl acetate/hexane/ethylether to afford 1.4 g of the desired product (white solid, yield: 81%).

M.P.: 198°–200° C.

¹H NMR (DMSO-d$_6$): δ 2.03(s, 3H), 2.40(s, 3H), 3.93(s, 3H), 4.10–4.50(m, 1H), 4.83–5.23(m, 1H), 6.26( s, 1H), 6.40–7.0(m, 1H), 7.26–7.73(m, 4H), 8.06–8.33(m, 1H), 9.13–9.46(m, 1H).

IR (KBr) ν (C=O) 1710 cm$^{-1}$

EXAMPLE 7

2-(2-fluoro-1-hydroxyethyl)-N-[(4-methoxy-6-methyl pyrimidin-2-yl)aminocarbonyl] benzenesulfonamide N-[(4-methoxy-6-methylpyrimidin-2-yl)amino carbonyl]-2-(1-acetoxy-2-fluoroethyl)benzenesulfonamide (1.4 g, 0.003 mol) was dissolved in 50 ml of tetrahydrofuran, and herein lithium hydroxide monohydride (0.4 g, 0.01 mol) and water were added.

After stirring for 12 hr at room temperature, the solution was diluted with 60 ml of water, and then conc-HCl was added dropwise at 0° C. to acidify the solution. The organic layer was obtained by adding 100 ml of methylene chloride, and the water layer was extracted with 60 ml of methylene chloride. The combined organic layer was dried, filtered and concentrated to obtain white solid.

This was washed with water and dried to afford 1.01 g of the desired product (white solid, yield: 89%).

M.P.: 153°–155° C.

¹H NMR (DMSO-d$_6$): δ 2.40(s, 3H), 3.93(s, 3H), 4.00–4.40(m, 1H), 4.73–5.13(m, 1H), 5.40–6.10(m, 1H), 6.33(s, 1H), 7.33–8.26(m, 5H), 9.23–9.56(m, 1H).

IR (KBr) ν (C=O) 1710 cm$^{-1}$

EXAMPLE 8

N-t-butyl-2-(2-fluoro-1-hydroxy-n-propyl) benzenesulfonamide (8-A, 8-B)

10 g of N-t-butyl-2-(2-fluoropropionyl) benzenesulfonamide prepared according to the example 1 was dissolved in 100 ml of methanol, and herein sodium 1.3 g of borohydride was added in the solution at room temperature.

After stirring the solution for 30 min at 40° C., methanol was concentrated and the obtained residue was dissolved in 100 ml of methylene chloride, washed with 5% HCl solution.

The separated organic layer was dried, filtered and concentrated to obtain a residue of oil type. The residue was chromatographed through silical gel using 1:6 (v/v) of ethyl acetate/hexane as eluant, and then 3.5 g of nonpolar compound (8-A) and polar compound (8-B) of 6 g were obtained as the desired product.

[Compound 8-A]

¹H NMR(200 MHz, CDCl$_3$): δ 1.24(s, 9H), 1.36(dd, 3H, J$_{H-H}$=6.4 Hz, J$_{H-F}$=25.3Hz), 2.94(br s, 1H), 4.80–5.27(m, 2H), 5.66–5.77(m,1H), 7.36–7.83(m, 3H), 8.03–8.10(m, 1H).

R$_f$=0.49 (ethyl acetate:hexane (v/v)=1:2)

[Compound 8-B]

¹H NMR(200 MHz, CDCl₃): δ 1.24(s, 9H), 1.36(dd, 3H, $J_{H-H}$=6.4 Hz, $J_{H-F}$=25.3 Hz), 3.01(br s, 1H), 4.83–5.25(m, 2H), 5.45–5.60(m,1H), 7.35–7.70(m, 3H), 8.03–8.10(m, 1H).

$R_f$=0.42 (ethyl acetate:hexane (v/v)=1:2)

EXAMPLE 9

2-(1-acetoxy-2-fluoro-n-propyl)-N-t-butyl benzenesulfonamide (9-A, 9-B)

Compound 8-A (3.5 g) according to the example 8 was dissolved in methylene chloride (50 ml), and herein actic anhydride (1.25 ml), pyridine (1.1 ml) and N,N-dimethylaminopyridine (0.12 g) were added in the solution.

After stirring at room temperature for 24 hr, the reaction solution was washed with 5% HCl solution, and the seperated organic layer was dried with magnesium sulfate, filtered and concentrated.

The obtained residue was chromatographed through silica gel using 1:3 (v/v) of ethyl acetate/hexane to afford the desired compound 9-A (white solid, 3.7 g).

[Compound 9-A]

M.P.: 126°–127° C.

¹H NMR (200 MHz, CDCl₃): δ 1.23(s, 9H), 1.36(dd, 3H, $J_{H-H}$=6.4 Hz, $J_{H-F}$=23.6 Hz), 2.18(s, 3H), 4.73–5.11(m, 1H), 5.54(br s, 1H), 6.49(dd, 1H, $J_{H-H}$=3.8 Hz, $J_{H-F}$=21.6 Hz), 7.41–7.69(m, 3H), 8.02–8.11(m, 1H)

IR (KBr) ν (C=O) 1715 cm⁻¹

The desired compound 9-B (6.4 g) was obtained from the compound 8-B (6 g) according to the example 8 by the same process with the above.

[Compound 9-B]

M.P.: 134°–135° C.

¹H NMR (200 MHz, CDCl₃): δ 1.25(s, 9H), 1.36(dd, 3H, $J_{H-H}$=6.4 Hz, $J_{H-F}$=25.3 Hz), 2.17(s, 3H), 4.86–5.22(m, 1H), 5.47(br s, 1H), 6.68(dd, 1H, $J_{H-H}$=3 Hz, $J_{H-F}$=18.6 Hz), 7.41–7.71(m, 3H), 8.04–8.12(m, 1H)

IR (KBr) ν (C=O) 1715 cm⁻¹

EXAMPLE 10

2-(1-acetoxy-2-fluoro-n-propyl)benzenesulfonamide (10-A, 10-B)

Compound 9-A (3.7 g) according to the example 9 was dissolved in 20 ml of trifluoroacetic acid, and stirred at room temperature for 24 hr.

After concentrating under the reduced temperature, the residue was dissolved in 50 ml of methylene chloride, and the solution was washed one time with 20 ml of 5% HCl solution.

The seperated organic layer was dired with magnesium sulfate, filtered and concentrated, and the residue was chromatographed with ethyl acetate/hexane to afford the desired compound 10-A (white, 2.3 g).

[Compound 10-A]

M.P.: 105°–107° C.

¹H NMR (200 MHz, CDCl₃): δ 1.33(dd, 3H, $J_{H-H}$=6.4 Hz, $J_{H-F}$=24.6 Hz), 2.18(s, 3H), 4.85–5.23(m, 1H), 5.55(br s, 2H), 6.53–6.68(m, 1H), 7.46–7.75(m, 3H), 8.06–8.13(m, 1H)

3.9 g of the desired compound 10-B (white solid) was obtained from the compound 9-B (6.4 g) according to the example 9 by the same process with the above.

[Compound 10-B]

M.P.: 126°–128° C.

¹H NMR (200 MHz, CDCl₃): δ 1.36(dd, 3H, $J_{H-H}$=6.4 Hz, $J_{H-F}$=24.2 Hz), 2.18(s, 3H), 4.75–5.12(m, 1H), 5.57(br s, 2H), 6.38–6.53(m, 1H), 7.46–7.66(m, 3H), 8.06–8.13(m, 1H)

EXAMPLE 11

2-(1-acetoxy-2-fluoro-n-propyl)-N-[(4,6-dimethoxypyrimidin-2-yl)aminocarbonyl] benzenesulfonamide (11-A, 11-B)

The compound 10-A (2.3 g) according to the example 10 was dissolved in 20 ml of acetonitrile, and herein 2.3 g of phenyl 4,6-dimethoxy-pyrimidin-2-yl carbamate was added at room temperature.

After adding dropwise 1 ml of DBU and stirring for 30 min, the reacted solution was diluted with 100 ml of methylene chloride, and was acidified with 50 ml of 5% HCl.

The seperated organic layer was washed with 50 ml of water, and dried with magnesium sulfate, filtered and concentrated.

The residue was treated with ethyl acetate/hexane/ethyl ether to afford the desired compound 11-A (white solid, 2.9 g).

[Compound 11-A]

M.P.: 191°–193° C.

¹H NMR (200 MHz, CDCl₃): δ 1.33(dd, 3H, $J_{H-H}$=6.4 Hz, $J_{H-F}$=24.6 Hz), 2.04(s, 3H), 3.96(s, 6H), 4.86–5.25(m, 1H), 5.80(s, 1H), 6.70–6.82(m, 1H), 7.18–7.70(m, 4H), 8.30–8.40(m, 1H), 13.15(br s, 1H)

The desired compound 11-B (white solid, 5.3 g) was obtained from the compound 10-B (3.9 g) according to the example 10 by the same process with the above.

[Compound 11-B]

M.P.: 194°–196° C.

¹H NMR (200 MHz, CDCl₃): δ 1.33(dd, 3H, $J_{H-H}$=6.4 Hz, $J_{H-F}$=24.2 Hz), 2.04(s, 3H), 3.96(s, 6H), 4.80–5.14(m, 1H), 5.80(s, 1H), 6.42–6.62(m, 1H), 7.23–7.70(m, 4H), 8.27–8.37(m, 1H), 12.95(br s, 1H)

EXAMPLE 12

N-[(4,6-dimethoxypyrimidin-2-yl)aminocarbonyl]-2-(2-fluoro-1-hydroxy-n-propyl)benzenesulfonamide (12-A, 12-B)

The compound 11-A (2.9 g) according to the example 11 was dissolved in 60 ml of tetrahydrofuran, and herein 0.9 g of lithium hydroxide monohydrate and 10 ml of water were added.

After stirring at room temperature for 12 hr, the reacted solution was diluted with 10 ml of water, and was acidified by dropwise addition of conc-HCl at 0° C.

The reaction mixture was extracted with 100 ml of ethyl acetate, and then water layer was extracted one more time.

The combined organic layer was dried with magnesium sulfate, filtered and concentrated to obtain white solid.

This was washed with ethylether to afford the desired compound 12-A (2.3 g).

[Compound 12-A]

M.P.: 166°–168° C.

¹H NMR (200 MHz, CDCl₃): δ 1.33(dd, 3H, $J_{H-H}$=6.4 Hz, $J_{H-F}$=24.6 Hz), 3.08(br s, 1H), 3.96(s, 6H), 4.86–5.25(m, 1H), 5.80(s, 1H), 5.89–6.07(m, 1H), 7.36–8.24(m, 5H), 12.82(br s 1H)

IR (KBr) ν (C=O) 1705 cm⁻¹

The desired compound 12-B (white solid, 3.0 g) was obtained from the compound 11-B (3.7 g) according to the example 11 by the same process with the above.

[Compound 12-B]
M.P.: 189°–191° C.
$^1$H NMR (200 MHz, CDCl$_3$): δ 1.36(dd, 3H, J$_{H-H}$=6.4 Hz, J$_{H-F}$=24.2 Hz), 3.96(s, 6H), 4.78–5.11 (m, 1H), 5.80(s, 1H), 5.79–5.91(m, 1H), 7.22–7.78(m, 4H), 8.13–8.22(m, 1H), 12.75(br s, 1H)
IR (KBr) ν (C=O) 1691 cm$^{-1}$

EXAMPLE 13

| Wettable Powder | |
|---|---|
| N-[(4,6-dimethoxypyrimidin-2-yl)aminocarbonyl]-2-(1-hydroxy-2-fluoroethyl)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 14

| Wettable Powder | |
|---|---|
| 2-(1-hydroxy-2-fluoroethyl)-N-[(4-methoxy-6-methylpyrimidin-2-yl)amino carbonyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 15

| Granule | |
|---|---|
| wettable powder of Example 14 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender.

The granules are dried and packaged.

EXAMPLE 16

| Extruded Pellet | |
|---|---|
| N-[(4,6-dimethoxypyrimidin-2-yl)aminocarbonyl]-2-(1-hydroxy-2-fluoroethyl)benzenesulfonamide | 25% |
| anhydrous sodium sulfate | 10% |
| crude calcium lignisulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. They may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 17

| Oil Suspension | |
|---|---|
| N-[(4,6-dimethoxypyrimidin-2-yl)aminocarbonyl]-2-(1-hydroxy-2-fluoroethyl)benzenesulfonamide | 25% |
| polyoxyethylene sorbitol hexaoleate | 5% |
| highly aliphatic hydrocarbon oil | 70% |

The ingredients are ground together in sand mill until the solid particles have been reduced to under about 5 microns. The resulting thick suspension may be applied directly, but preferably after being extended with oils or emulsified in water.

EXAMPLE 18

| Wetting Powder | |
|---|---|
| N-[(4,6-dimethoxypyrimidin-2-yl)aminocarbonyl]-2-(1-hydroxy-2-fluoroethyl)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm openings) and packaged.

EXAMPLE 19

| Low Strength Granule | |
|---|---|
| N-[(4,6-dimethoxypyrimidin-2-yl)aminocarbonyl]-2-(1-hydroxy-2-fluoroethyl)benzenesulfonamide | 1% |
| N,N-dimethylformamide | 9% |
| attapulgite granule (U.S.S. 20–40 sieve) | 90% |

The active ingredient is dissolved in the solvent and the solution is sprayed upon dedusted granules in a double cone blender.

After spraying of the solution has been completed, the blender is allowed to run for a short period and then the granules are packaged.

EXAMPLE 20

| Aqueous Suspension | |
|---|---|
| N-[(4,6-dimethoxypyrimidin-2-yl)aminocarbonyl]-2-(1-hydroxy-fluoroethyl)benzenesulfonamide | 40% |
| polyacrylic acid thickener | 0.3% |
| dodecylphenol polyethylen glycol ether | 0.5% |
| disodium phosphate | 1% |
| monosodium phosphate | 0.5% |
| polyvinyl alcohol | 1% |
| water | 56.7% |

The ingredients are blended and ground together in a sand mill to produce particles essentially all under 5 microns in size.

EXAMPLE 21

| Solution | |
|---|---|
| N-[(4,6-dimethoxypyrimidin-2-yl)aminocarbonyl]-2-(1-hydroxy-2-fluoroethyl)benzenesulfonamide | 5% |
| water | 95% |

The salt is added directly to the water with stirring to produce the solution, which may then be packaged for use.

EXAMPLE 22

| Low Strength Granule | |
|---|---|
| N-[(4,6-dimethoxypyrimidin-2-yl)aminocarbonyl]-2-(1-hydroxy-2-fluoroethyl)benzenesulfonamide | 0.1% |
| attapulgite granules (U.S.S. No. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and packaged.

EXAMPLE 23

| Wettable Powder | |
|---|---|
| N-[(4,6-dimethoxypyrimidin-2-yl)aminocarbonyl]-2-(1-hydroxy-2-fluoroethyl)benzenesulfonamide | 40% |
| dioctyl sodium sulfosuccinate | 1.5% |
| sodium ligninsulfonate | 3% |
| low viscosity methyl cellulose | 1.5% |
| attapulgite | 54% |

The ingredient are throughly blended, passed through an air mill, to produce an average particle size under 15 microns, reblended, and sifted through a U.S.S. No. 50 sieve (0.3 mm opening) before packaging. All compounds of the invension may be formulated in the same manner.

EXAMPLE 24

| Granule | |
|---|---|
| wettable powder of Example 23 | 15% |
| gypsum | 69% |
| potassium sulfate | 16% |

The ingredients are blended in rotating mixer and water sprayed on to accomplish granulation. When most of the material has reached the desired range of 1.0 to 0.42 cm (U.S.S. #18 to 40 sieves), the granules are removed, dried, and screened. Oversized material is crushed additional material in the desired range. These granules contain % active ingredient.

EXAMPLE 25

| High Strength Concentrate | |
|---|---|
| N-[(4,6-dimethoxypyrimidin-2-yl)aminocarbonyl]-2-(1-hydroxy-2-fluoroethyl)benzenesulfonamide | 99% |
| silica aerogel | 0.5% |
| synthetic amorphous silica | 0.5% |

The ingredient are blended and ground in a hammer-mill to produce a material essentially all passing a U.S.S. No. 50 screen (0.3 mm opening). The concentrate may be formulated further if necessary.

EXAMPLE 26

| Wettable Powder | |
|---|---|
| N-[(4,6-dimethoxypyrimidin-2-yl)aminocarbonyl]-2-(1-hydroxy-2-fluoroethyl)benzenesulfonamide | 90% |
| dioctyl sodium sulfosuccinate | 0.1% |
| synthetic fine silica | 9.9% |

The ingredient are blended and ground in a hammer-mill to produce particles essentially all below 100 microns. The material is sifted through a U.S.S. No. 50 screen and the packaged.

EXAMPLE 27

| Wettable Powder | |
|---|---|
| N-[(4,6-dimethoxypyrimidin-2-yl)aminocarbonyl]-2-(1-hydroxy-2-fluoroethyl)benzenesulfonamide | 40% |
| sodium ligninsulfonate | 20% |
| montmorillonite clay | 40% |

The ingredients are throughly blended, coarsely hammer-milled and then air-milled to produce particles essentially all below 10 microns in size. The material is reblended and the packaged.

EXAMPLE 28

| Oil Suspension | |
|---|---|
| N-[(4,6-dimethoxypyrimidin-2-yl)aminocarbonyl]-2-(1-hydroxy-2-fluoroethyl)benzenesulfonamide | 35% |
| blended of polyalcohol carboxylic ester and oil soluble petroleum sulfonate | 6% |
| xylene | 59% |

The ingredients are combined and ground together in a sand mill to produce particle essentially all below 5 microns. The product can be used directly, extended with oil, or emulsified in water.

EXAMPLE 29

| Dust | |
|---|---|
| N-[(4,6-dimethoxypyrimidin-2-yl)aminocarbonyl]-2-(1-hydroxy-2-fluoroethyl)benzenesulfonamide | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 30

| Emulsifiable Concentrate | |
|---|---|
| N-[(4,6-dimethoxypyrimidin-2-yl)aminocarbonyl]-2-(1-hydroxy-2-fluoroethyl)benzenesulfonamide | 10% |
| chlorobenzene | 84% |
| sorbitan monostearate and polyoxyethylene condensates thereof | 6% |

The ingredients are combined and stirred to produce a solution which can be emulsified in water for application.

EXAMPLE 31

Pre-emergence test

To produce a suitable preparation of active compound, 1 part by weight of active compound is mixed with 5 parts by weight of acetone, 1 part by weight of alkylaryl polyglycol ether of emulsifier is added and the concentrate is diluted with water to the desired concentration Seeds of the test plants are shown in normal soil and, after 24 hours, watered with the preparation of the active compound.

It is expedient to keep constant the amount of water per unit area. The concentration of the active compound in the preparation is of no importance, only the amount of active compound applied per unit area being desicive. After three weeks, the degree of damage to the plants is rated in % damage in comparison to the development of the untreated control.

The figures denote:

| | |
|---|---|
| 0% = | no action (like untreated control) |
| 20% = | slight effect |
| 70% = | herbicidal effect |
| 100% = | total destruction. |

In this test, the active compounds(I) according to the preparation Examples exhibit a better herbicidal activity against nomo- and dicotyledon weeds.

EXAMPLE 32

Post-emergence test

To produce a suitable preparation of active compound, 1 part by weight of active compound is mixed with 5 parts by weight of acetone, 1 part by weight of alkylaryl polyglycol ether of emulsifier is added and the concentrate is diluted with water to the desired concentration.

Test plants which have a height of 5~15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparasion to the development of the untreated control.

The figures denote:

| | |
|---|---|
| 0% = | no action (like untreated control) |
| 20% = | slight effect |
| 70% = | herbicidal effect |
| 100% = | total destruction. |

In this test, the active compounds(I) according to the preparation Examples exhibit a better herbicidal activity against mono- and dicotyledon weeds.

It is understood that the specification and examples are illustrative but not limitative of the present invention and that other embodiments within the spirit and scope of the invention will suggest themselves to those skilled in the art.

The herbicidal proficiency of the active ingredients of the present invention is evident from the test results which are recorded in following Tables.

The following Tables are represented pre- and post-emergence herbicidal evaluation [PRIMARY SCREENING (Herbicide)] of following "test compounds".

| Structure | X | Y | Compound No. |
|---|---|---|---|
| (structure with OH, F, SO$_2$NHCONH-pyrimidine) | OCH$_3$<br>CH$_3$<br>CH$_3$ | OCH$_3$<br>OCH$_3$<br>CH$_3$ | 1<br>2<br>3 |
| (structure with OH, F, SO$_2$NHCONH-pyrimidine) | OCH$_3$<br>OCH$_3$<br>CH$_3$ | OCH$_3$<br>OCH$_3$<br>OCH$_3$ | 4 (high mp)<br>5 (low mp)<br>6 |

-continued

| Structure | X | Y | Compound No. |
|---|---|---|---|
| [Structure with OH, CH2CH2F, SO2NHCONH-pyrimidine] | OCH3<br>CH3 | OCH3<br>OCH3 | 7<br>8 |
| [Structure with OH, CH2Cl, SO2NHCONH-pyrimidine] | OCH3<br>CH3 | OCH3<br>CH3 | 9<br>10 |
| [Structure with OH, CHClCH3, SO2NHCONH-pyrimidine] | CH3<br>CH3 | OCH3<br>CH3 | 11<br>12 |
| [Structure with OH, CHF2, SO2NHCONH-pyrimidine] | OCH3<br>CH3 | OCH3<br>OCH3 | 13<br>14 |
| [Structure with OH, CH2F, SO2NHCONH-triazine] | OCH3 | OCH3 | 15 |

PLANT RESPONSE SCREENING (Herbicide)

| Comp. No. | TYPE | kg/ha | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|
| 1 | PRE | .05 | 100 | 100 | 90 | 100 | 100 | 65 | 90 | 90 | 90 | 100 |
|   | POST | .05 | 100 | 100 | 100 | 100 | 100 | 70 | 100 | 100 | 100 | 100 |
| 2 | PRE | .05 | 100 | 100 | 100 | 100 | 100 | 50 | 100 | 90 | 100 | 100 |
|   | POST | .05 | 100 | 100 | 100 | 100 | 100 | 20 | 100 | 80 | 100 | 100 |
| 3 | PRE | .05 | 100 | 100 | 90 | 65 | 100 | 60 | 25 | 40 | 35 | 90 |
|   | POST | .05 | 100 | 100 | 100 | 55 | 100 | 60 | 90 | 20 | 100 | 90 |
| 4 | PRE | .05 | 100 | 100 | [15] | 100 | 100 | 50 | 80 | 90 | 90 | 100 |
|   | POST | .05 | 90 | 100 | [50] | 100 | 100 | 30 | 100 | 70 | 100 | 100 |
| 5 | PRE | 2 | 100 | 100 | [100] | 100 | 100 | 90 | 100 | 85 | 100 | 100 |
|   | POST | 2 | 100 | 100 | [95] | 100 | 100 | 100 | 100 | 100 | 100 | 100 |
| 6 | PRE | .05 | 100 | 100 | [25] | 100 | 100 | 65 | 60 | 40 |  | 100 |
|   | POST | .05 | 70 | 90 | [50] | 90 | 100 | 15 | 90 | 25 | 90 | 100 |
| 7 | PRE | .05 | 100 | 100 | [60] | 100 | 100 | 60 | 80 | 90 | 90 | 100 |
|   | POST | .05 | 100 | 100 | [65] | 100 | 100 | 50 | 100 | 100 | 100 | 100 |
| 8 | PRE | .05 | 100 | 100 | [80] | 100 | 100 | 60 | 90 | 90 |  | 100 |

PLANT RESPONSE SCREENING (Herbicide)

| Comp. No. | TYPE | kg/ha | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|
| | POST | .05 | 65 | 90 | [65] | 100 | 100 | 25 | 100 | 45 | 100 | 100 |
| 9 | PRE | .05 | 100 | 90 | [20] | 60 | 100 | 65 | 70 | 60 | | 100 |
| | POST | .05 | 70 | 80 | [30] | 25 | 75 | 20 | 100 | 35 | 100 | 100 |
| 10 | PRE | .05 | 0 | 0 | [0] | 0 | 0 | 0 | 0 | 0 | 0 | 0 |
| | POST | .05 | 0 | 0 | [0] | 0 | 0 | 0 | 0 | 0 | 0 | 0 |
| 11 | PRE | 4 | 80 | 80 | [40] | 90 | 90 | 50 | 0 | 50 | 60 | 70 |
| | POST | 4 | 50 | 90 | [40] | 60 | 70 | 45 | 30 | 80 | 60 | 100 |
| 13 | PRE | .05 | 100 | 90 | (60) | 100 | 100 | | 80 | 90 | 80 | 100 |
| | POST | .05 | 70 | 100 | (70) | 60 | 100 | | 100 | 100 | 100 | 80 |
| 14 | PRE | .05 | 100 | 100 | (80) | 100 | 100 | | 70 | 90 | 85 | 100 |
| | POST | .05 | 60 | 80 | (60) | 50 | 100 | | 80 | 40 | 70 | 100 |
| 15 | PRE | .05 | 50 | 50 | 0 | 20 | | 20 | 0 | 0 | 0 | 30 |
| | POST | .05 | 40 | 60 | 0 | 20 | 100 | 60 | 20 | 0 | 20 | 40 |

PRIMARY SCREENING (Herbicide)

| Comp. No. | TYPE | kg/ha | ZEAMX | GLXMX | GOSHI | TRZAW | ORYSA | SORBI | ECHOR | BROJA (SETVI) [AGRSM] | DIGSA | PANDI | SOLNI |
|---|---|---|---|---|---|---|---|---|---|---|---|---|---|
| 1 | PRE | .1 | 100 | 100 | 100 | 50 | 100 | 100 | 100 | (100) | 100 | 100 | 50 |
| | | .05 | 100 | 100 | 100 | 20 | 100 | 100 | 100 | (100) | 100 | 100 | 40 |
| | | .025 | 100 | 100 | 100 | 10 | 100 | 100 | 100 | (100) | 100 | 100 | 20 |
| | | .0125 | 65 | 70 | 80 | 0 | 100 | 100 | 100 | (100) | 100 | 100 | 0 |
| | | .006 | 40 | 65 | 60 | 0 | 90 | 100 | 100 | (90) | 100 | 100 | 0 |
| | POST | .1 | 100 | 100 | 100 | 40 | 100 | 100 | 100 | (100) | 100 | 100 | 40 |
| | | .05 | 100 | 100 | 60 | 30 | 100 | 100 | 100 | (100) | 100 | 100 | 30 |
| | | .025 | 70 | 100 | 40 | 0 | 70 | 100 | 100 | (100) | 100 | 100 | 30 |
| | | .0125 | 60 | 100 | 0 | 0 | 60 | 100 | 100 | (100) | 80 | 100 | 0 |
| | | .006 | 40 | 100 | 0 | 0 | 40 | 100 | 100 | (30) | 20 | 100 | 0 |
| 2 | PRE | 1 | | 100 | 90 | 100 | 100 | 100 | 100 | 100 | 100 | 100 | 90 |
| | | .05 | | 100 | 90 | 90 | 100 | 100 | 100 | 100 | 100 | 100 | 60 |
| | | .025 | | 90 | 90 | 60 | 100 | 100 | 100 | 100 | 100 | 100 | 50 |
| | | .012 | | 80 | 80 | 40 | 100 | 100 | 100 | 90 | 100 | 100 | 50 |
| | | .006 | | 80 | 70 | 20 | 100 | 90 | 100 | 70 | 100 | 100 | 50 |
| | POST | .1 | 100 | 100 | 80 | 100 | 100 | 100 | 100 | 100 | 100 | 100 | 70 |
| | | .05 | 100 | 100 | 80 | 100 | 100 | 80 | 100 | 100 | 100 | 100 | 70 |
| | | .025 | 100 | 90 | 75 | 40 | 100 | 80 | 100 | 100 | 100 | 100 | 60 |
| | | .012 | 100 | 90 | 60 | 30 | 100 | 80 | 100 | 100 | 90 | 100 | 50 |
| | | .006 | 100 | 90 | 60 | 20 | 100 | 80 | 100 | 100 | 80. | 100 | 50 |
| 3 | PRE | .1 | 100 | 50 | 50 | 40 | 100 | 100 | 100 | (100) | 100 | 100 | 70 |
| | | .05 | 100 | 40 | 40 | 30 | 100 | 100 | 100 | (50) | 100 | 100 | 50 |
| | | .025 | 40 | 30 | 0 | 10 | 100 | 100 | 100 | (30) | 80 | 90 | 0 |
| | | .0125 | 0 | 0 | 0 | 0 | 50 | 100 | 40 | (0) | 40 | 70 | 0 |
| | | .006 | 0 | 0 | 0 | 0 | 30 | 90 | 0 | (0) | 0 | 0 | 0 |
| | POST | .1 | 80 | 60 | 70 | 60 | 100 | 100 | 100 | (100) | 100 | 100 | 50 |
| | | .05 | 60 | 40 | 50 | 40 | 100 | 100 | 100 | (50) | 30 | 80 | 50 |
| | | .025 | 40 | 30 | 30 | 30 | 90 | 40 | 40 | (20) | 0 | 30 | 30 |
| | | .0125 | 0 | 20 | 0 | 0 | 80 | 0 | 20 | (0) | 0 | 0 | 20 |
| | | .006 | 0 | 20 | 0 | 0 | 60 | 0 | 0 | (0) | 0 | 0 | 0 |
| 4 | PRE | 1 | 100 | 90 | 100 | 0 | 100 | 100 | 100 | [60] | 100 | 100 | 90 |
| | | .025 | 50 | 50 | 40 | 0 | 40 | 100 | 80 | [30] | 80 | 100 | 50 |
| | | .00625 | 20 | 20 | 0 | 0 | 0 | 50 | 40 | [0] | 30 | 80 | 0 |
| | | .001562 | 0 | 0 | 0 | 0 | 0 | 0 | 0 | [0] | 0 | 30 | 0 |
| | | .00039 | 0 | 0 | 0 | 0 | 0 | 0 | 0 | [0] | 0 | 0 | 0 |
| | POST | .1 | 70 | 100 | 60 | 30 | 50 | 100 | 100 | [40] | 100 | 100 | 70 |
| | | .025 | 50 | 100 | 30 | 0 | 30 | 100 | 60 | [20] | 40 | 100 | 40 |
| | | .00625 | 30 | 70 | 0 | 0 | 0 | 70 | 0 | [0] | 30 | 70 | 30 |
| | | .001562 | 0 | 40 | 0 | 0 | 0 | 0 | 0 | [0] | 0 | 20 | 0 |
| | | .00039 | 0 | 0 | 0 | 0 | 0 | 0 | 0 | [0] | 0 | 0 | 0 |
| 5 | PRE | .1 | 100 | 100 | 100 | 20 | 100 | 100 | 100 | [70] | 100 | 100 | 70 |
| | | .025 | 100 | 90 | 100 | 0 | 100 | 100 | 100 | [60] | 100 | 100 | 60 |
| | | .00625 | 50 | 70 | 50 | 0 | 50 | 100 | 100 | [40] | 100 | 100 | 60 |
| | | .00156 | 0 | 20 | 0 | 0 | 0 | 50 | 60 | [0] | 60 | 100 | 40 |
| | | .00039 | 0 | 0 | 0 | 0 | 0 | 0 | 0 | [0] | 40 | 100 | 0 |
| | POST | .1 | 100 | 100 | 70 | 40 | 50 | 100 | 100 | [70] | 100 | 100 | 100 |
| | | .025 | 100 | 100 | 40 | 0 | 30 | 100 | 100 | [50] | 100 | 100 | 60 |
| | | .00625 | 90 | 90 | 20 | 0 | 10 | 70 | 100 | [20] | 60 | 100 | 50 |
| | | .00156 | 20 | 50 | 0 | 0 | 0 | 50 | 50 | [0] | 0 | 80 | 50 |
| | | .00039 | 0 | 40 | 0 | 0 | 0 | 0 | 0 | [0] | 0 | 20 | 40 |
| 7 | PRE | .1 | 100 | 100 | 100 | 30 | 100 | 100 | 100 | [80] | 100 | 100 | 70 |

5,736,628

-continued

PRIMARY SCREENING (Herbicide)

| | | | | | | | | | | | | | |
|---|---|---|---|---|---|---|---|---|---|---|---|---|---|
| | | .025 | 50 | 80 | 100 | 0 | 100 | 100 | 100 | [65] | 100 | 100 | 70 |
| | | .00625 | 40 | 50 | 40 | 0 | 90 | 100 | 70 | [30] | 70 | 100 | 40 |
| | | .001562 | 0 | 20 | 0 | 0 | 60 | 30 | 0 | [0] | 30 | 30 | 30 |
| | | .00039 | 0 | 0 | 0 | 0 | 0 | 0 | 0 | [0] | 0 | 0 | 0 |
| | POST | .1 | 90 | 100 | 60 | 40 | 100 | 100 | 100 | [100] | 100 | 100 | 80 |
| | | .025 | 50 | 100 | 40 | 0 | 100 | 100 | 100 | [60] | 100 | 100 | 60 |
| | | .00625 | 0 | 80 | 0 | 0 | 60 | 80 | 80 | [30] | 40 | 100 | 50 |
| | | .001562 | 0 | 60 | 0 | 0 | 20 | 80 | 20 | [0] | 0 | 60 | 20 |
| | | .00039 | 0 | 20 | 0 | 0 | 0 | 40 | 0 | [0] | 0 | 50 | 0 |
| 8 | PRE | .1 | 100 | 100 | 100 | 70 | 100 | 100 | 100 | [80] | 100 | 100 | 90 |
| | | .025 | 100 | 100 | 100 | 50 | 100 | 100 | 100 | [80] | 100 | 100 | 90 |
| | | .00625 | 70 | 70 | 100 | 30 | 100 | 80 | 90 | [50] | 100 | 90 | 70 |
| | | .001562 | 0 | 40 | 40 | 0 | 50 | 60 | 50 | [30] | 40 | 50 | 40 |
| | | .00039 | 0 | 0 | 0 | 0 | 0 | 0 | 0 | [0] | 0 | 0 | 0 |
| | POST | .1 | 100 | 100 | 90 | 60 | 100 | 100 | 100 | [70] | 100 | 100 | 80 |
| | | .025 | 70 | 100 | 70 | 40 | 100 | 100 | 100 | [50] | 100 | 100 | 60 |
| | | .00625 | 40 | 90 | 50 | 30 | 60 | 50 | 60 | [20] | 40 | 20 | 50 |
| | | .001562 | 0 | 40 | 0 | 0 | 30 | 20 | 30 | [0] | 20 | 0 | 40 |
| | | .00039 | 0 | 20 | 0 | 0 | 0 | 0 | 0 | [0] | 0 | 0 | 0 |
| 13 | PRE | .1 | 90 | 90 | 100 | 0 | 100 | 100 | 100 | (70) | 100 | 100 | 50 |
| | | .025 | 70 | 65 | 65 | 0 | 90 | 80 | 80 | (60) | 90 | 100 | 30 |
| | | .00625 | 20 | 20 | 50 | 0 | 40 | 40 | 65 | (20) | 60 | 80 | 0 |
| | | .00156 | 0 | 0 | 50 | 0 | 0 | 0 | 0 | (0) | 20 | 60 | 0 |
| | POST | .1 | 80 | 100 | 60 | 0 | 80 | 100 | 100 | (65) | 90 | 100 | 40 |
| | | .025 | 70 | 80 | 40 | 0 | 50 | 50 | 80 | (30) | 40 | 100 | 0 |
| | | .00625 | 30 | 40 | 40 | 0 | 30 | 50 | 40 | (0) | 0 | 80 | 0 |
| | | .00156 | 0 | 40 | 20 | 0 | 0 | 40 | 0 | (0) | 0 | 0 | 0 |
| 14 | PRE | .1 | 90 | 100 | 100 | 30 | 100 | 100 | 100 | (70) | 100 | 100 | 50 |
| | | .025 | 50 | 65 | 90 | 0 | 90 | 50 | 90 | (50) | 90 | 90 | 30 |
| | | .00625 | 0 | 20 | 60 | 0 | 40 | 30 | 65 | (20) | 70 | 70 | 0 |
| | | .00156 | 0 | 0 | 40 | 0 | 0 | 0 | 50 | (0) | 50 | 70 | 0 |
| | POST | .1 | 90 | 70 | 65 | 0 | 90 | 40 | 80 | (60) | 50 | 70 | 40 |
| | | .025 | 30 | 50 | 20 | 0 | 40 | 20 | 40 | (0) | 20 | 20 | 0 |
| | | .00625 | 0 | 20 | 0 | 0 | 0 | 0 | 0 | (0) | 0 | 0 | 0 |
| | | .00156 | 0 | 0 | 0 | 0 | 0 | 0 | 0 | (0) | 0 | 0 | 0 |

| Comp. No. | TYPE | kg/ha | AESIN | ABUTH | XANSI | CAGHE |
|---|---|---|---|---|---|---|
| 1 | PRE | .1 | 100 | 100 | 100 | 100 |
| | | .05 | 70 | 100 | 90 | 100 |
| | | .025 | 40 | 90 | 90 | 100 |
| | | .0125 | 20 | 60 | 80 | 100 |
| | | .006 | 0 | 30 | 70 | 100 |
| | POST | .1 | 100 | 100 | 100 | 100 |
| | | .05 | 100 | 100 | 100 | 100 |
| | | .025 | 100 | 100 | 100 | 100 |
| | | .0125 | 70 | 70 | 70 | 100 |
| | | .006 | 70 | 50 | 20 | 100 |
| 2 | PRE | 1 | 80 | 100 | 100 | 100 |
| | | .05 | 80 | 100 | 100 | 100 |
| | | .025 | 65 | 90 | 100 | 100 |
| | | .012 | 40 | 80 | 90 | 100 |
| | | .006 | 30 | 70 | 80 | 100 |
| | POST | .1 | 100 | 100 | 100 | 100 |
| | | .05 | 100 | 100 | 100 | 100 |
| | | .025 | 100 | 65 | 100 | 100 |
| | | .012 | 100 | 50 | 100 | 100 |
| | | .006 | 80 | 50 | 100 | 100 |
| 3 | PRE | .1 | 30 | 40 | 60 | 100 |
| | | .05 | 0 | 30 | 40 | 100 |
| | | .025 | 0 | 20 | 20 | 100 |
| | | .0125 | 0 | 0 | 0 | 50 |
| | | .006 | 0 | 0 | 0 | 40 |
| | POST | .1 | 70 | 60 | 70 | 100 |
| | | .05 | 60 | 20 | 50 | 100 |
| | | .025 | 40 | 0 | 0 | 100 |
| | | .0125 | 0 | 0 | 0 | 100 |
| | | .006 | 0 | 0 | 0 | 100 |
| 4 | PRE | 1 | 60 | 100 | 100 | 100 |
| | | .025 | 20 | 50 | 65 | 100 |
| | | .00625 | 0 | 0 | 30 | 90 |
| | | .001562 | 0 | 0 | 0 | |
| | | .00039 | 0 | 0 | 0 | 0 |
| | POST | .1 | 100 | 100 | 100 | 100 |
| | | .025 | 90 | 40 | 90 | 80 |
| | | .00625 | 40 | 0 | 40 | 30 |
| | | .001562 | 0 | 0 | 0 | 0 |
| | | .00039 | 0 | 0 | 0 | 0 |

| PRIMARY SCREENING (Herbicide) | | | | | | |
|---|---|---|---|---|---|---|
| 5 | PRE | .1 | 90 | 90 | 100 | 100 |
| | | .025 | 30 | 65 | 100 | 100 |
| | | .00625 | 0 | 40 | 90 | 80 |
| | | .00156 | 0 | 0 | 70 | 50 |
| | | .00039 | 0 | 0 | 40 | 0 |
| | POST | .1 | 100 | 100 | 100 | 100 |
| | | .025 | 60 | 100 | 100 | 100 |
| | | .00625 | 50 | 40 | 100 | 90 |
| | | .00156 | 20 | 0 | 80 | 40 |
| | | .00039 | 0 | 0 | 30 | 0 |
| 7 | PRE | .1 | 100 | 100 | 100 | 100 |
| | | .025 | 40 | 80 | 100 | 100 |
| | | .00625 | 0 | 30 | 50 | 50 |
| | | .001562 | 0 | 0 | 0 | 20 |
| | | .00039 | 0 | 0 | 0 | 0 |
| | POST | .1 | 100 | 100 | 100 | 100 |
| | | .025 | 100 | 40 | 100 | 100 |
| | | .00625 | 60 | 30 | 60 | 40 |
| | | .001562 | 0 | 0 | 40 | 30 |
| | | .00039 | 0 | 0 | 0 | 0 |
| 8 | PRE | .1 | 100 | 100 | 100 | 100 |
| | | .025 | 100 | 100 | 100 | 100 |
| | | .00625 | 80 | 60 | 100 | 100 |
| | | .001562 | 20 | 40 | 40 | 100 |
| | | .00039 | 0 | 0 | 0 | 40 |
| | POST | .1 | 100 | 70 | 100 | 100 |
| | | .025 | 90 | 0 | 100 | 90 |
| | | .00625 | 50 | 0 | 80 | 40 |
| | | .001562 | 0 | 0 | 20 | 20 |
| | | .00039 | 0 | 0 | 0 | 0 |
| 13 | PRE | .1 | 40 | 90 | 100 | 100 |
| | | .025 | 20 | 70 | 100 | 100 |
| | | .00625 | 0 | 0 | 40 | 40 |
| | | .00156 | 0 | 0 | 0 | 0 |
| | POST | .1 | 100 | 100 | 100 | 70 |
| | | .025 | 80 | 100 | 100 | 60 |
| | | .00625 | 40 | 40 | 50 | 0 |
| | | .00156 | 0 | 0 | 20 | 0 |
| 14 | PRE | .1 | 60 | 90 | 100 | 100 |
| | | .025 | 30 | 40 | 100 | 100 |
| | | .00625 | 0 | 0 | 40 | 100 |
| | | .00156 | 0 | 0 | 0 | 40 |
| | POST | .1 | 80 | 70 | 100 | 100 |
| | | .025 | 50 | 40 | 20 | 60 |
| | | .00625 | 0 | 0 | 0 | 20 |
| | | .00156 | 0 | 0 | 0 | 0 |

| PRIMARY SCREENING (PADDY SUBMERGED)-Herbicide | | | | | | | | | |
|---|---|---|---|---|---|---|---|---|---|
| Comp. No. | DAT | kg/ha | ORYSA (3 Leaf) | ORYSA (seed) | ECHOR | SCPJU | MOOVA | CYPSE | SAGPY |
| 1 | 2 | .05 | 90 | 90 | 100 | 100 | 100 | 100 | 100 |
| 2 | 2 | .05 | 90 | 90 | 80 | 100 | 100 | 100 | 70 |
| | | .1 | 90 | 100 | 100 | 100 | 100 | 100 | 90 |
| | | .025 | 90 | 90 | 90 | 100 | 90 | 100 | 80 |
| | | .006 | 70 | 60 | 60 | 100 | 80 | 100 | 70 |
| | | .0015 | 20 | 10 | 0 | 50 | 70 | 50 | 40 |
| | | .0004 | 0 | 0 | 0 | 0 | 60 | 0 | 0 |
| 3 | 2 | .05 | 70 | 60 | 60 | 50 | 70 | 60 | 60 |
| 4 | 2 | .05 | 60 | 70 | 90 | 90 | 90 | 100 | 90 |
| | | .05 | 60 | 90 | 100 | 100 | 100 | 100 | 100 |
| | | .025 | 50 | 50 | 90 | 90 | 100 | 100 | 100 |
| | | .0125 | 40 | 50 | 70 | 70 | 100 | 100 | 100 |
| | | .006 | 30 | 20 | 30 | 30 | 100 | 100 | 100 |
| | | .003 | 0 | 0 | 0 | 0 | 100 | 100 | 100 |
| | | .005 | 0 | 30 | 0 | 90 | 0 | 100 | 100 |
| | | .0025 | 0 | 0 | 0 | 40 | 0 | 90 | 90 |
| | | .00125 | 0 | 0 | 0 | 0 | 0 | 50 | 70 |
| | | .00063 | 0 | 0 | 0 | 0 | 0 | 30 | 50 |
| | | .00031 | 0 | 0 | 0 | 0 | 0 | 0 | 0 |
| 5 | 3 | .01 | 0 | 80 | 100 | | 100 | 100 | 100 |
| | | .005 | 0 | 50 | 100 | | 90 | 100 | 100 |
| | | .0025 | 0 | 0 | 90 | | 90 | 100 | 100 |
| | | .0012 | 0 | 0 | 70 | | 80 | 70 | 100 |

-continued

PRIMARY SCREENING (PADDY SUBMERGED)-Herbicide

| Comp. No. | DAT | kg/ha | ORYSA (3 Leaf) | ORYSA (seed) | ECHOR | SCPJU | MOOVA | CYPSE | SAGPY |
|---|---|---|---|---|---|---|---|---|---|
|  |  | .00062 | 0 | 0 | 20 |  | 70 | 40 | 95 |
| 6 | 2 | .05 | 60 | 60 | 60 | 80 | 40 | 100 | 80 |
| 7 | 2 | .05 | 90 | 100 | 100 | 100 | 100 | 100 | 100 |
|  |  | .05 | 100 | 100 | 100 | 100 | 100 | 100 | 100 |
|  |  | .025 | 90 | 100 | 100 | 90 | 100 | 100 | 100 |
|  |  | .0125 | 80 | 90 | 100 | 80 | 100 | 100 | 100 |
|  |  | .006 | 80 | 80 | 40 | 70 | 100 | 100 | 100 |
|  |  | .003 | 50 | 50 | 20 | 30 | 100 | 100 | 100 |
|  | 3 | .05 | 90 | 100 | 100 | 95 | 95 | 100 | 100 |
|  |  | .0125 | 30 | 10 | 30 | 30 | 60 | 95 | 100 |
|  |  | .003 | 0 | 0 | 0 | 0 | 0 | 0 | 60 |
|  |  | .00078 | 0 | 0 | 0 | 0 | 0 | 0 | 0 |
|  |  | .0002 | 0 | 0 | 0 | 0 | 0 | 0 | 0 |
| 8 | 2 | .05 | 70 | 90 | 90 | 90 | 90 | 100 | 90 |
|  |  | .05 | 80 | 90 | 100 | 80 | 100 | 100 | 100 |
|  |  | .025 | 80 | 80 | 100 | 80 | 100 | 100 | 100 |
|  |  | .0125 | 70 | 60 | 40 | 30 | 100 | 60 | 100 |
|  |  | .006 | 40 | 40 | 30 | 0 | 90 | 60 | 90 |
|  |  | .003 | 20 | 20 | 0 | 0 | 90 | 30 | 70 |
| 9 | 2 | .05 | 70 | 90 | 90 | 90 | 90 | 100 | 90 |
|  |  | .05 | 60 | 70 | 90 | 70 | 100 | 100 | 100 |
|  |  | .025 | 50 | 60 | 70 | 30 | 100 | 100 | 100 |
|  |  | .0125 | 30 | 40 | 40 | 0 | 100 | 100 | 100 |
|  |  | .006 | 30 | 20 | 0 | 0 | 80 | 100 | 100 |
|  |  | .003 | 20 | 0 | 0 | 0 | 50 | 80 | 80 |
| 10 | 2 | .05 | 0 | 0 | 0 | 0 | 0 | 0 | 0 |
| 11 | 2 | .05 | 0 | 0 | 50 | 0 | 0 | 20 | 0 |
| 12 | 2 | .05 | 10 | 10 | 40 | 40 | 40 | 60 | 60 |
| 13 | 2 | .05 | 60 | 60 | 90 | 70 | 80 | 30 | 90 |
|  | 3 | .1 | 100 | 90 | 100 | 100 | 100 | 100 | 100 |
|  |  | .025 | 70 | 70 | 100 | 100 | 100 | 50 | 90 |
|  |  | .006 | 40 | 40 | 80 | 40 | 60 | 0 | 90 |
|  |  | .0015 | 10 | 0 | 40 | 0 | 30 | 0 | 80 |
|  |  | .0004 | 0 | 0 | 20 | 0 | 0 | 0 | 0 |
| 14 | 2 | .05 | 50 | 60 | 70 | 50 |  | 90 | 80 |
|  | 3 | .1 | 70 | 90 | 100 | 90 | 100 | 100 | 90 |
|  |  | .025 | 40 | 50 | 90 | 50 | 60 | 60 | 90 |
|  |  | .006 | 0 | 30 | 30 | 20 | 0 | 30 | 40 |
|  |  | .0015 | 0 | 0 | 0 | 0 | 0 | 0 | 0 |
|  |  | .0004 | 0 | 0 | 0 | 0 | 0 | 0 | 0 |
| 15 | 2 | .05 | 40 | 50 | 0 | 0 | 50 | 0 | 60 |

What is claimed is:
1. A compound of benzenesulfonylurea derivatives having the following general formula (I)

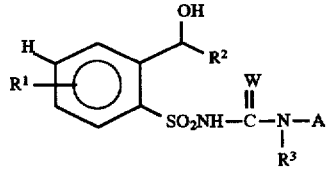

(I)

wherein,
$R^1$ is H, $C_1$–$C_3$ alkyl, $C_1$–$C_3$ haloalkyl, halogen, CN, $NO_2$, $C_1$–$C_3$ alkoxy, $C_1$–$C_3$ haloalkoxy, $SO_2NR^IR^{II}$, $C_1$–$C_3$ alkylthio, $C_1$–$C_3$ alkylsulfinyl, $C_1$–$C_3$ alkylsulfonyl, $SCH_2F$, $NH_2$, $NHCH_3$, $N(Me)_2$, $C_1$–$C_2$ alkyl substituted with $C_1$–$C_2$ alkoxy, $C_1$–$C_2$ haloalkoxy, SH, $SCH_3$, CN or OH, or $CO_2R^{III}$; and then $R^I$ is H, $C_1$–$C_4$ alkyl, $C_2$–$C_3$ cyanoalkyl, methoxy or ethoxy; $R^{II}$ is H, $C_1$–$C_4$ alkyl, $C_3$–$C_4$ alkenyl, or when taken together connecting $R^I$ and $R^{II}$, —$(CH_2)_3$—, —$(CH_2)_4$—, —$(CH_2)_5$— or $CH_2CH_2OCH_2CH_2$—, may be formed;
$R^{III}$ is $C_1$–$C_4$ alkyl, $C_3$–$C_4$ alkenyl, $C_3$–$C_4$ alkynyl, $C_1$–$C_4$ alkyl substituted with 1–3 halogens or cyano groups, $C_5$–$C_6$ cycloalkyl, $C_3$–$C_7$ cycloalkylalkyl or $C_2$–$C_4$ alkoxyalkyl;

$R^2$ is $C_1$–$C_6$ alkyl substituted with 1–3 halogens;
$R^3$ is H or $CH_3$;
W is O or S;
A is

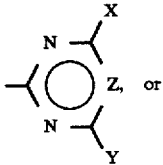

A1 or

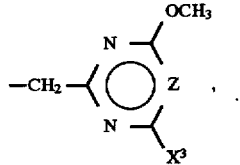

A6 wherein,
X is H, $C_1$–$C_4$alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino, di($C_1$–$C_3$ alkyl)amino or $C_3$–$C_5$ cycloalkyl;

Y is H, $C_1$-$C_4$ alkyl, $C_1$-$C_4$ alkoxy, $C_1$-$C_4$ haloalkoxy, $C_1$-$C_4$ haloakylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_4$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_2$-$C_4$ alkynyl, azido, cyano, $C_2$-$C_5$ alkylsulfinylalkyl, $C_2$-$C_5$ alkylsulfonylalkyl, $CH_2OH$, $C_3$-$C_5$ cycloalkyl, $C_3$-$C_5$ cycloalkoxy,

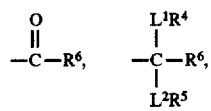

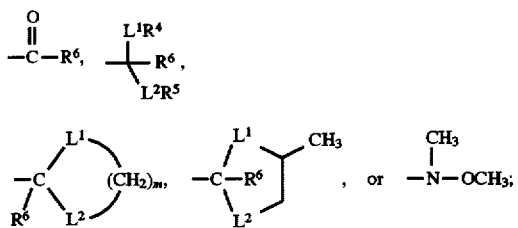, or —N—OCH$_3$;

m is 2 or 3;

$L^1$ and $L^2$ are independently O or S;

$R^4$ and $R^5$ are independently $C_1$-$C_2$ alkyl;

$R^6$ is H, or $CH_3$;

$X^3$ is $CH_3$ or $OCH_3$;

or the agriculturally suitable salt thereof.

2. A compound as defined in the claim 1, wherein W is O, and $R^3$ is H.

3. A compound as defined in the claim 1, wherein $R^1$ is selected from the group consisting of H, halogen, $C_1$-$C_2$ alkyl, $C_1$-$C_2$ alkoxy, $C_1$-$C_2$ haloalkyl, $C_1$-$C_2$ alkylthio, haloalkoxy and $CH_2CN$; X is selected from the group consisting of $C_1$-$C_2$ alkyl, $C_1$-$C_2$ alkoxy, Cl, F, Br, I, $OCHF_2$, $CH_2F$, $CF_3$, $OCH_2CH_2F$, $OCH_2CHF_2$, $OCH_2CF_3$, $CH_2Cl$ and CH2Br; and Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

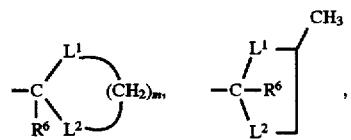

$OCHF_2$, $OCF_2Br$, $SCHF_2$, cyclopropyl, C≡CH or C≡C—$CH_3$, and then $R^4$ and $R^5$ are $C_1$-$C_2$ alkyl, $R^6$ is H or $CH_3$, $L^1$ and $L^2$ are O or S, and m is 2 or 3.

4. A compound as defined in the claim 1, wherein $R^2$ is $CH_2F$, $CH_2CH_2F$, $CHFCH_3$, $CH_2Cl$, $CH_2Br$, $CHCl_2$, $CHFCl$, $CH_2CH_2Cl$, $CHClCH_3$, $CHF_2$, $CHClCH_2Cl$, $CHFCH_2Cl$, $CHFCH_2F$ or $CH_2CHF_2$.

5. An intermediate compound of the formula (I) in claim 1 having the following general formula (II)

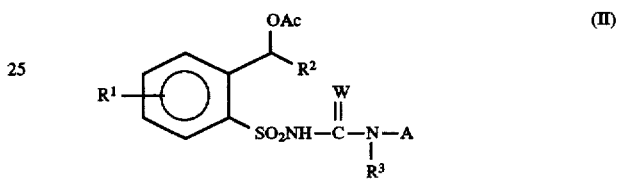

wherein R1, R2, R3, W and A are respectively as defined in the above claim 1; and Ac is an acetyl group or protecting group which regenerates hydroxy under acid or alkali conditions.

6. A compound as defined in claim 5, wherein $R^1$ is H; $R^2$ is $CH_2F$, $CH_2Cl$, $CHF_2$, $CHFCH_3$ or $CH_2CH_2F$; $R^3$ is H; A is $A_1$; and W is O.

* * * * *

UNITED STATES PATENT AND TRADEMARK OFFICE
CERTIFICATE OF CORRECTION

PATENT NO. : 5,736,628                    Page 1 of 6
DATED      : 7 April 1998
INVENTOR(S): Dae-Whang KIM et al.

It is certified that error appears in the above-identified patent and that said Letters Patent is hereby corrected as shown below:

| Column | Line | |
|---|---|---|
| 1 | 60 | Change "-CHR-CN" to<br>$\phantom{xx}\vert$<br>$\phantom{xx}R^{16}$<br><br>-- -CH-CN etc ($R^{16}$ is alkyl);--.<br>$\phantom{xx}\vert$<br>$\phantom{xx}R^{16}$ |
| 2 | 65 | Change "cycloalky." to --cycloalkyl.--. |
| 5 | 20 | Change "buthyl" to --butyl--. |
| 5 | 24 | Change "buthenyl" to --butenyl--. |
| 5 | 27 | Change "buthenyl" to --butenyl--. |
| 5 | 31 | Change "pyridine" to --benzene--. |
| 5 | 33 | Change "compounding of the polymer" to --easiness of synthesis--. |
| 5 | 45 | Change "$OCH_2CH\equiv CH$," to --$OCH_2C\equiv CH$,--. |
| 2 | 65 | $C_3 - C_6-$ to $C_5 - C_6$ |

UNITED STATES PATENT AND TRADEMARK OFFICE
CERTIFICATE OF CORRECTION

PATENT NO. : 5,736,628
DATED : 7 April 1998
INVENTOR(S) : Dae-Whang KIM et al.

It is certified that error appears in the above-identified patent and that said Letters Patent is hereby corrected as shown below:

| Column | Line | |
|---|---|---|
| 5 | 58 | Change "compounding of the polymer" to --easiness of synthesis--. |
| 6 | 9 | Change "1-hydroxypropyl)" to --1-hydroxy-n-propyl)--. |
| 6 | 12 | Change "high m.p. (189~191°C.)" to --low m.p. (166~168°C.)--. |
| 6 | 13 | Change "low m.p. (166°-168°C.)." to --high m.p. (189°~191°C.).--. |
| 8 | 14 | Change "Other" to --other--. |
| 10 | 4 | Change "Sinolin" to --Smolin--. |
| 27 | 27 | Change "pro-emergent" to --pre-emergent--. |
| 27 | 37 | After "modify" delete "," |
| 29 | 38 | Change "metharn" to --metham--. |
| 30 | 56 | Change "dissolved in 2" to --dissolved in 20--. |

UNITED STATES PATENT AND TRADEMARK OFFICE
CERTIFICATE OF CORRECTION

PATENT NO. : 5,736,628
DATED : 7 April 1998
INVENTOR(S) : Dae-Whang KIM et al.

It is certified that error appears in the above-identified patent and that said Letters Patent is hereby corrected as shown below:

| Column | Line | |
|---|---|---|
| 31 | 37 | Before "N-[4,6-dimethoxy..." insert --2-(1-Acetoxy-2-flouroethyl)--. |
| 31 | 38 | Change "acetoxy-2-fluoroethyl" to --aminocarbonly]--. |
| 31 | 52 | Change "181°=173°C." to --180°-181°C.--. |
| 32 | 5 | Change "chlomatographed" to --treated--. |
| 32 | 21 | Before "N-[(4-methoxy-t..." insert -- 2-(1-Acetoxy-2-fluoroethyl)- --. |
| 32 | 22 | Delete "-2-(1-acetoxy-2-fluoroethyl)". |
| 32 | 48 | After "benzenesulfonamide" delete to end of line. |
| 32 | 49 | After "herein" delete "sodium". |
| 32 | 50 | Change "borohydride" to --sodiumborohydride--. |
| 32 | 60 | Before "polar" insert --6g of--; after "(8-B)" delete "of 6g". |

UNITED STATES PATENT AND TRADEMARK OFFICE
CERTIFICATE OF CORRECTION

PATENT NO. : 5,736,628
DATED : 7 April 1998
INVENTOR(S) : Dae-Whang KIM et al.

It is certified that error appears in the above-identified patent and that said Letters Patent is hereby corrected as shown below:

| Column | Line | |
|---|---|---|
| 33 | 53 | Change "dired" to --dried--. |
| 35 | 13 | Change "(1-hydroxy-2-fluoroethyl)" to --(2-fluoro-1-hydroxyethyl)--. |
| 35 | 27 | Change "(1-hydroxy-2-fluoroethyl)" to --(2-fluoro-1-hydroxyethyl)--. |
| 35 | 56-57 | Change "(1-hydroxy-2-fluoroethyl)" to --(2-fluoro-1-hydroxyethyl)--. |
| 36 | 9-10 | Change "(1-hydroxy-2-fluoroethyl)" to --(2-fluoro-1-hydroxyethyl)--. |
| 36 | 24-25 | Change "(1-hydroxy-2-fluoroethyl)" to --(2-fluoro-1-hydroxyethyl)--. |

UNITED STATES PATENT AND TRADEMARK OFFICE
CERTIFICATE OF CORRECTION

PATENT NO. : 5,736,628

DATED : 7 April 1998

INVENTOR(S) : Dae-Whang KIM et al.

It is certified that error appears in the above-identified patent and that said Letters Patent is hereby corrected as shown below:

| Column | Line | |
|---|---|---|
| 36 | 40-41 | Change "(1-hydroxy-2-fluoroethyl)" to --(2-fluoro-1-hydroxyethyl)--. |
| 36 | 56-57 | Change "(1-hydroxy-2-fluoroethyl)" to --(2-fluoro-1-hydroxyethyl)--. |
| 37 | 5-6 | Change "(1-hydroxy-2-fluoroethyl)" to --(2-fluoro-1-hydroxyethyl)--. |
| 37 | 19-20 | Change "(1-hydroxy-2-fluoroethyl)" to --(2-fluoro-1-hydroxyethyl)--. |
| 37 | 36-37 | Change "(1-hydroxy-2-fluoroethyl)" to --(2-fluoro-1-hydroxyethyl)--. |
| 38 | 5-6 | Change "(1-hydroxy-2-fluoroethyl)" to --(2-fluoro-1-hydroxyethyl)--. |

UNITED STATES PATENT AND TRADEMARK OFFICE
CERTIFICATE OF CORRECTION

PATENT NO. : 5,736,628
DATED : 7 April 1998
INVENTOR(S) : Dae-Whang KIM et al.

It is certified that error appears in the above-identified patent and that said Letters Patent is hereby corrected as shown below:

| Column | Line  |                                                                    |
|--------|-------|--------------------------------------------------------------------|
| 38     | 22-23 | Change "(1-hydroxy-2-fluoroethyl)" to --(2-fluoro-1-hydroxyethyl)--. |
| 38     | 39-40 | Change "(1-hydroxy-2-fluoroethyl)" to --(2-fluoro-1-hydroxyethyl)--. |
| 38     | 56-57 | Change "(1-hydroxy-2-fluoroethyl)" to --(2-fluoro-1-hydroxyethyl)--. |
| 39     | 5-6   | Change "(1-hydroxy-2-fluoroethyl)" to --(2-fluoro-1-hydroxyethyl)--. |
| 39     | 20-21 | Change "(1-hydroxy-2-fluoroethyl)" to --(2-fluoro-1-hydroxyethyl)--. |
| 51     | 35    | Change "CH2Br" to --$CH_2Br$--.                                     |

Signed and Sealed this

Fourth Day of May, 1999

*Attest:*

Q. TODD DICKINSON

*Attesting Officer*   Acting Commissioner of Patents and Trademarks